(12) United States Patent
Karaoguz et al.

(10) Patent No.: US 10,110,677 B2
(45) Date of Patent: Oct. 23, 2018

(54) CONTEXT-AWARE DECISION MAKING

(71) Applicant: BROADCOM CORPORATION, Irvine, CA (US)

(72) Inventors: Jeyhan Karaoguz, Irvine, CA (US); Marcus Christopher Kellerman, Poway, CA (US); John Stuart Walley, Ladera Ranch, CA (US); James Duane Bennett, Hroznětín (CZ); Xuemin Chen, Rancho Santa Fe, CA (US); Bradley Donald Blanche, Aliso Viejo, CA (US)

(73) Assignee: AVAGO TECHNOLOGIES GENERAL IP (SINGAPORE) PTE. LTD., Singapore (SG)

( * ) Notice: Subject to any disclaimer, the term of this patent is extended or adjusted under 35 U.S.C. 154(b) by 741 days.

(21) Appl. No.: 14/543,771

(22) Filed: Nov. 17, 2014

(65) Prior Publication Data
US 2015/0324698 A1   Nov. 12, 2015

Related U.S. Application Data

(60) Provisional application No. 61/989,358, filed on May 6, 2014.

(51) Int. Cl.
*H04L 29/08* (2006.01)
*G06N 5/04* (2006.01)
(Continued)

(52) U.S. Cl.
CPC .............. *H04L 67/12* (2013.01); *G06F 3/015* (2013.01); *G06N 5/04* (2013.01); *G16H 50/50* (2018.01);
(Continued)

(58) Field of Classification Search
None
See application file for complete search history.

(56) References Cited

U.S. PATENT DOCUMENTS

2004/0122297 A1* 6/2004 Stahmann ............ A61B 5/0031
600/300
2012/0117006 A1* 5/2012 Sathish ............... G06F 11/3072
706/12
(Continued)

FOREIGN PATENT DOCUMENTS

WO   WO 2014018687 A1 *  1/2014  ......... G06F 17/2785

*Primary Examiner* — Alan Chen
(74) *Attorney, Agent, or Firm* — McDermott Will & Emery LLP

(57) ABSTRACT

A context-aware decision making system may include at least one processor circuit that is configured to obtain an environmental profile of an environment associated with a user. The at least one processor circuit is configured to determine a predicted behavior of the user based at least on the obtained environmental profile. The at least one processor circuit may be configured to determine the predicted behavior of the user using at least one predictive model associated with the user. The at least one processor circuit may be configured to perform an action related to the predicted behavior of the user, such as an action that facilitates the predicted behavior of the user, an action that impedes the predicted behavior of the user, and/or an action that provides information related to the predicted behavior of the user.

50 Claims, 11 Drawing Sheets

(51) Int. Cl.
*G06F 3/01* (2006.01)
*G16H 50/50* (2018.01)
*G06F 19/00* (2018.01)

(52) U.S. Cl.
CPC ............ H04L 67/22 (2013.01); H04L 67/306 (2013.01); *G06F 19/3475* (2013.01)

(56) References Cited

U.S. PATENT DOCUMENTS

| | | | | |
|---|---|---|---|---|
| 2012/0249797 A1* | 10/2012 | Haddick | ................ | G06F 1/163 |
| | | | | 348/158 |
| 2014/0032572 A1* | 1/2014 | Eustice | ............... | G06F 17/2785 |
| | | | | 707/748 |
| 2014/0171039 A1* | 6/2014 | Bjontegard | ....... | H04L 29/06034 |
| | | | | 455/414.1 |
| 2014/0347265 A1* | 11/2014 | Aimone | ................ | G09G 3/003 |
| | | | | 345/156 |
| 2015/0262208 A1* | 9/2015 | Bjontegard | ........ | G06Q 30/0202 |
| | | | | 705/7.31 |
| 2015/0294085 A1* | 10/2015 | Kare | .................... | G06F 19/322 |
| | | | | 705/3 |

* cited by examiner

CONTEXT-AWARE DECISION MAKING

CROSS-REFERENCE TO RELATED APPLICATIONS

The present application claims the benefit of U.S. Provisional Patent Application Ser. No. 61/989,358, entitled "Context-Aware Behavioral Feedback," filed on May 6, 2014, which is hereby incorporated by reference in its entirety for all purposes.

TECHNICAL FIELD

The present description relates generally to devices that provide decision making, and devices that provide context-aware decision making and/or behavioral feedback.

BACKGROUND

According to some estimates, more than 30 billion devices will be capable of being connected by 2020. These devices may include sensor devices, wearable devices, computing devices, home appliances, and the like. The devices may be configurable to interoperate with one or more other devices, such as to collectively perform one or more tasks, e.g. on behalf of a user and/or an application.

BRIEF DESCRIPTION OF THE DRAWINGS

Certain features of the subject technology are set forth in the appended claims. However, for purpose of explanation, several embodiments of the subject technology are set forth in the following figures.

DETAILED DESCRIPTION

Figure 1:
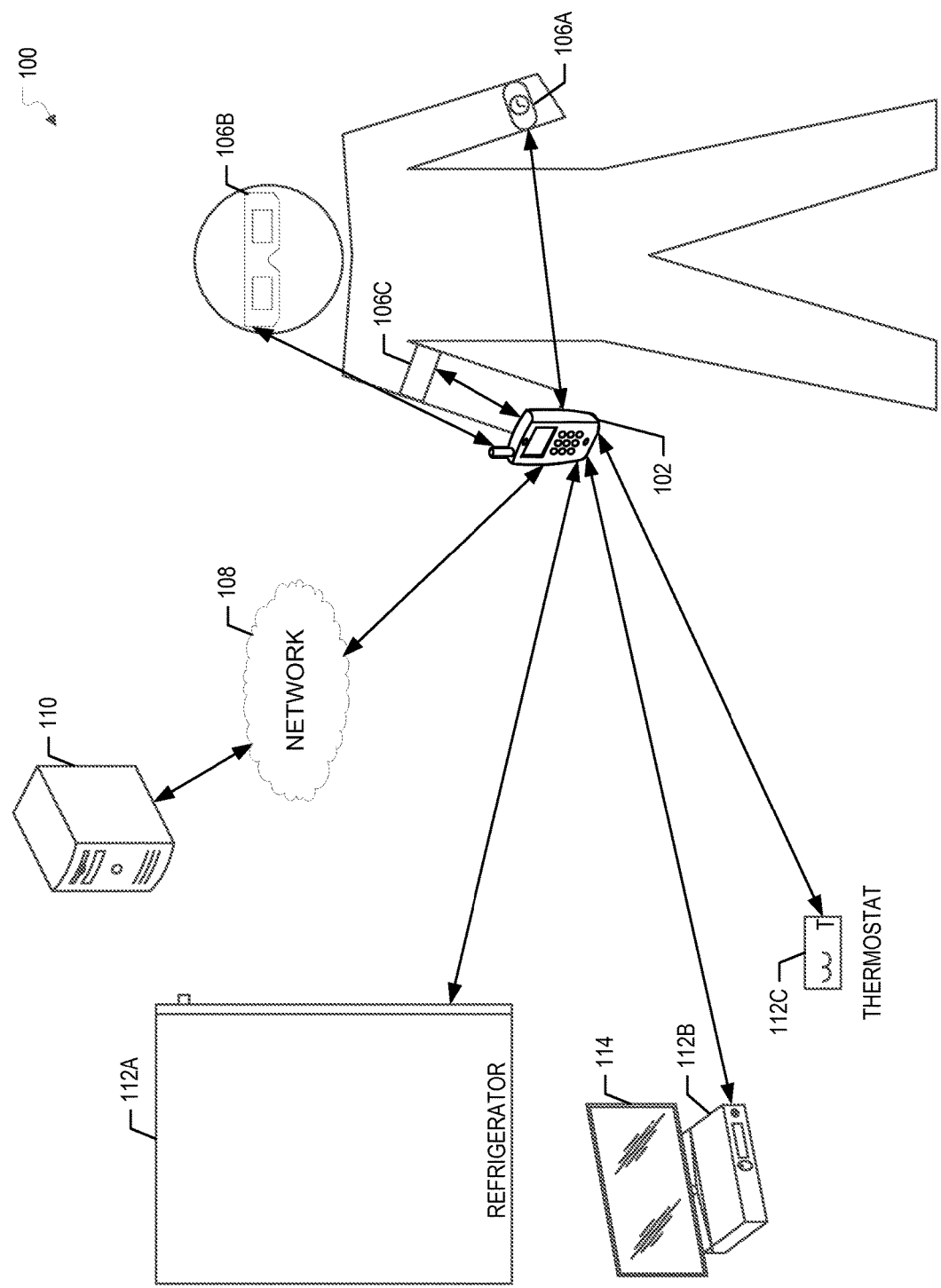
FIG. 1 illustrates an example network environment in which a context-aware decision making system may be implemented in accordance with one or more implementations.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced using one or more implementations. In one or more instances, structures and components are shown in block diagram form in order to avoid obscuring the concepts of the subject technology.

The subject context-aware decision making system collects and/or obtains information regarding one or more users' behaviors, biometric data, and/or associated environmental information over a period of time. The associated environmental information may include, for example, a discrete and/or descriptive location of the user, such as in a kitchen of the user's home, a time of day, information regarding one or more devices that are proximal to the user, such as a refrigerator device, and the like. The users' behaviors may include online behaviors, such as submitting a query to a search engine, and/or offline behaviors, such as eating breakfast. In one or more implementations, the subject system uses the collected information to determine predicted and/or expected behaviors of a user, such as based at least on obtainable current environmental information associated with the user and/or obtainable current biometric data of the user. The subject system performs context-aware decision making to determine an action that facilitates the predicted and/or expected behavior of the user, such as providing context-aware behavioral feedback and/or other information to the user that relates to the predicted and/or expected behavior, and/or initiating performance of an action that relates to the predicted and/or expected behavior. In one or more implementations, the subject system receives a behavioral policy that is intended to guide behaviors of a user, such as a dietary policy, and the subject system performs actions to conform predicted and/or expected behaviors of the user to behaviors indicated by the behavioral policy.

The subject system uses the collected information to determine predicted and/or expected biometric data for a user, such as based at least on obtainable or detectable current environmental information associated with the user, and/or obtainable or detectable current behaviors of the user. The system collects and/or monitors the current biometric data of the user and determines whether the current biometric data deviates from the predicted and/or expected biometric data. If the current biometric data deviates from the predicted and/or expected biometric data, the subject system provides context-aware decision making by performing an action that facilitates conforming the current biometric data of the user to the predicted and/or expected biometric data of the user. If the current biometric data conforms to the predicted and/or expected biometric data, the subject system may perform an action to facilitate maintaining the current biometric data for the user.

FIG. 1 illustrates an example network environment 100 in which a context-aware decision making system may be implemented in accordance with one or more implementations. Not all of the depicted components may be used, however, and one or more implementations may include additional components not shown in the figure. Variations in the arrangement and types of the components may be made without departing from the spirit or scope of the claims as set forth herein. Additional, different or fewer components may be provided.

The network environment 100 includes an electronic device 102, a network 108, one or more electronic sensor devices 106A-C, one or more electronic devices 112-C, an output device 114, and a service provider server 110. The network 108 may include, and/or may be communicatively coupled to, one or more of the Internet, a private network, a personal area network, and/or any other networks. The network 108 may include one or more wired or wireless network devices that facilitate communications of the electronic device 102, the electronic devices 112A-C, and/or the service provider server 110, such as switch devices, router devices, relay devices, etc., and/or the network 108 may include one or more server devices. The electronic device 102 may establish a direct network connection, e.g. via Bluetooth, near-field communication (NFC), WiFi Direct, etc., with one or more of the electronic devices 112A-C and/or one or more of the electronic sensor devices 106A-C, without communicating through the network 108. The electronic sensor devices 106A-C are each capable of communicating both directly and indirectly with the electronic device 102. Indirectly both via the access points of the network 108 and via other of the electronic sensor devices 106A-C, e.g., via meshes or relaying. In one or more implementations, one or more of the electronic sensor devices 106A-C may be directly communicatively coupled to the network 108.

The electronic device 102 is depicted in FIG. 1 as a smartphone. However, the electronic device 102 may be any network-connectable device that can receive sensor data, such as from one or more of the electronic sensor devices 106A-C. In one or more implementations, the electronic device 102 is, and/or includes, one or more of the electronic sensor devices 106A-C, such as an accelerometer, a heart rate measurement device, etc. The electronic device 102 may include a secure element for storing user biometric information, biometric profiles, environmental profiles, predictive models, etc. The electronic device 102 may aggregate data received from one or more of the electronic sensor devices 106A-C, and/or from one or more of the electronic devices 112A-C, to generate one or more biometric profiles and/or one or more environmental profiles for a user.

The electronic sensor device 106A is depicted in FIG. 1 as a smart watch, the electronic sensor device 106B is depicted in FIG. 1 as smart glasses, and the electronic sensor device 106C is depicted in FIG. 1 as an arm band device. However, the electronic sensor devices 106A-C may be any devices that can obtain, or sense, information regarding a user and/or an environment associated with the user, such as biometric information, user activity information, user images, temperature, location, time of day, etc. For example, the electronic sensor devices 106A-C may include network camera devices, home security devices, heart rate monitoring devices, implanted and/or implantable devices, wearable devices, activity monitoring devices, blood flow monitoring devices, sleep monitoring devices, or generally any device that can provide information from which a user is identifiable.

In one or more implementations, one or more of the electronic sensor devices 106A-C may be one or more of: a shoe insert device that measures weight changes of the user, such as while eating and visiting the restroom; a belt device that senses pressure changes from the user's body pressing on the belt device and that changes sizes to maintain a particular pressure with respect to the user's body, such as when the user gains and/or loses weight; or a scale device that provides the weight of the user. One or more of the electronic sensor devices 106A-C may include at least one processor circuit that can perform one or more processing tasks described herein.

In one or more implementations, one or more of the electronic sensor devices 106A-C, such as the electronic sensor device 106B, includes a secure element for storing user biometric information, biometric profiles, environmental profiles, predictive models, etc., e.g. in lieu of and/or in addition to, the electronic device 102. One or more of the electronic sensor devices 106A-C, such as the electronic sensor device 106B, may communicate directly with the network 108 and/or with one or more of the electronic devices 112A-C, without communicating through the electronic device 102.

The electronic devices 112A-C may be devices that are proximal or remote to the electronic device 102, and/or to the electronic sensor devices 106A-C, and that can provide information to, and/or perform instructed actions for, the electronic device 102 and/or the electronic sensor devices 106A-C. One or more of the electronic devices 112A-C may include one or more sensors and/or sensor devices, such as one or more of the sensor devices 106A-C, for sensing, observing, and/or obtaining information. The electronic device 112A is depicted in FIG. 1 as a refrigerator device, the electronic device 112B is depicted as a set-top box device that is communicatively coupled to an output device 114, such as a display, and the electronic device 112C is depicted as a thermostat device. However, the electronic devices 112A-C may be any devices that provide information to, and/or perform instructed actions for, the electronic device 102 and/or the electronic sensor devices 106A-C.

In one or more implementations, the electronic device 102 and/or one or more of the electronic sensor devices 106A-C includes an output device, such as a display and/or speakers, for providing context-aware behavioral feedback to a user. The electronic device 102 and/or one or more of the electronic sensor devices 106A-C may be configured to access, and/or provide context-aware behavioral feedback via, an output device associated with a communicatively coupled device, such as the output device 114 of the electronic device 112B.

The service provider server 110 may be one or more computing devices that that may operate in conjunction with the electronic device 102, and/or one or more of the electronic sensor devices 106A-C, to provide the context-aware decision making system. For example, the service provider server 110 may include one or more server devices and a database that securely stores user biometric information, profiles, models, etc., e.g. in lieu of and/or in addition to, the electronic device 102. One or more of the electronic device 102, the electronic sensor devices 106A-C, the service provider server 110, and/or the electronic devices 112A-C, may be, and/or may include all or part of, the electronic system illustrated in FIG. 7.

The network 108 may include a gateway device, such as the electronic device 112B, that facilitates communications of the electronic device 102, the electronic sensor devices 106A-C, the service provider server 110, and/or the electronic devices 112A-C. The electronic device 102 may operate as, and/or in conjunction with, the gateway device to facilitate providing a context-aware decision making system. The electronic device 112B may host at least a portion of the context-aware decision making system, e.g. in lieu of and/or in addition to the service provider server 110.

The electronic device 102 and/or the service provider server 110 may collect information over a period of time, such as via one or more of the electronic sensor devices 106A-C, that pertains to a user, such as one or more biometric data items that collectively form one or more biometric profiles of the user, information that describes behaviors and/or activities of the user, such as world interactions, sleeping, relaxing, working, stress activities, calm activities, and/or one or more environmental variables that form one or more environmental profiles, such as time of day, location of the user, weather information, information regarding devices proximal to the user, etc. The environmental variables and/or environmental profiles may be associated with one or more of the biometric profiles and/or the information describing the behaviors of the user. For example, the environmental profiles may describe environments in which the user is located when the biometric data items and/or the information describing the behaviors of the user is collected.

The aforementioned biometric profiles of the user may include one or more biometric data items collected instantaneously, and/or over a period of time, for the user, such as one or more biometric data items collected from the same and/or different electronic sensor devices 106A-C over a period of time. A biometric profile may include, and/or describe, a biological rhythm of the user. In one or more implementations, one or more of the biometric data items are biometric values measured from the user by one or more of the electronic sensor devices 106A-C, such as heart rate. One or more of the biometric data items may relate to moods of the user that are empirically measurable and/or observable by one or more of the electronic sensor devices 106A-C, such as a happy mood, a sad mood, etc. One or more of the biometric data items may relate to responses of the user that are empirically measurable and/or observable by the electronic sensor devices 106A-C, such as responses to one or more stimuli that may be described in an associated environmental profile.

In one or more implementations, the empirically determinable and/or observable moods and/or responses that relate to the biometric data items includes one or more pleasure moods/responses determinable from facial expressions, such as smiling, pleasure moods/responses determinable from verbal expressions, such as "ummm," and/or pleasure moods/responses determinable from any measurable biometric values. The empirically determinable and/or observable moods and/or responses may include one or more displeasure moods/responses determinable from facial expressions, such as frowning, displeasure moods/responses determinable from verbal expressions, such as "yuck," and/ or displeasure moods/responses determinable from any measurable biometric values.

The aforementioned environmental profiles of the user may include one or more environmental variables collected instantaneously, and/or over a period of time, with respect to the user, such as a descriptive and/or discrete location of the user, a time of day associated with the user, information regarding clothes being worn by the user and/or activities being engaged in by the user, a current weather associated with the user, information regarding one or more devices that are proximal to the user, or generally any environmental variables that describe and/or relate to an environment associated with the user. The descriptive and/or discrete location of the user may describe the environment associated with the user and/or the environment in which the user is located, such as in a kitchen, in a car, in a bedroom, etc.

The electronic device 102, the service provider server 110, and/or one or more of the electronic sensor devices 106A-C may continuously monitor and/or update a current biometric profile of the user and/or a current environmental profile of the user, irrespective of whether any requests have been received therefor. For example, the electronic device 102 and/or the service provider server 110 may continuously receive data from one or more of the electronic sensor devices 106A-C and/or the electronic devices 112A-C, and continuously update the current biometric profile of the user and/or the current environmental profile of the user with the received data.

The electronic device 102 and/or the service provider server 110 may use the collected information and/or profiles associated with the user, which is referred to as historical data, to predict behaviors of the user in order to provide context-aware behavioral feedback to the user, e.g. information that the user is interested in and/or actions that facilitate the user in performing the predicted behaviors. In one or more implementations, the electronic device 102, and/or the service provider server 110, generates one or more predictive models that are used to predict the behaviors of the user, such as based at least on the current environment in which the user is located. For example, when the user walks into a room, the electronic device 102 and/or the service provider server 110 determines context-aware behavioral feedback that is useful to the user, such as based at least on a predicted behavior of the user in the room, and/or actions that facilitate the user with performing a predicted behavior in the room.

The context-aware behavioral feedback provided by the electronic device 102 and/or the service provider server 110 may take many different forms. The feedback may be information provided for display to a user, the feedback may be used to perform an action on behalf of the user, initiate performance of an action on behalf of the user, reconfigure an application on behalf of a user, make a software selection on behalf of the user, such as based on the user's preferences and/or biometric profile, and/or the feedback may be any information that may be provided to the user and/or used to change, effect, or perform an action on behalf of the user.

In one or more implementations, if the user walks towards a picture window in the morning, and the user typically views weather information in the morning, the electronic device 102 predicts this user behavior before it occurs and provides a heads up display, such as via electronic sensor device 106B, and/or verbal communication of, the temperature and/or weather forecast for the day, such as retrieved from an online weather portal. The electronic device 102 may provide a suggestion to the user based at least on the weather forecast, such as to avoid barbeques when there is rain in the forecast.

If the user opens a refrigerator in the morning, such as the electronic device 112A, the electronic device 102 predicts this user behavior before it occurs and suggests to the user what is most likely to be pleasing for the user to cook/eat for breakfast, such as based at least on historical breakfast eating habits of the user, available food in the refrigerator (e.g., as provided by the electronic device 112A), and/or historical pleasurable and/or unpleasurable responses for recipes that can be made based at least on the available food.

The recipes may be provided by a recipe portal, such as a portal maintained by the service provider server 110.

In one or more implementations, when the electronic device 102 predicts that the user will and/or should eat soon, the electronic device 102 suggests food for the user to cook/eat based at least on diet offerings for the user and/or perishable dates of the available food. The refrigerator device, such as the electronic device 112A, and/or a cupboard device, may maintain catalogs of available food, such as by using an imager, radio frequency identification technology, and the like, and provides an indication of the available foods to the electronic device 102, such as when the electronic device 102 predicts that the user will and/or should eat soon. The electronic sensor device 106B may include a camera device that recognizes foods in the refrigerator device and/or reads and/or recognizes ingredients of recipes being prepared by the user, and the electronic sensor device 106B provides an indication of the recognized foods and/or ingredients to the electronic device 102. The electronic device 102 may operate in a full mode where a recipe is only suggested to the user when the full recipe can be met based at least on available food, and/or in a partial mode where a recipe is suggested to the user when one or more ingredients are missing and/or can be substituted with another available ingredient.

The electronic device 102 may filter the context-aware behavioral feedback provided to the user based at least on recent behaviors of the user, such as a recent activity level of the user. For example, if the user did not exercise recently, the electronic device 102 suggests that the user skip desert when the user is looking at ice cream. The electronic device 102 and/or the electronic sensor device 106B may use optical processing so that the ice cream is not visible to the user, and/or so that the ice cream looks like some other food that historically causes an unpleasurable response from the user. Thus, the electronic device 102 and/or the service provider server 110 identifies and store historical behaviors of the user (and/or other users) for a given environment, such as described by the location, time of day, etc., and uses the stored information to predict behaviors in a similar environment in the future and provide context-aware behavioral feedback associated therewith. An example process of providing context-aware behavioral feedback based at least on predicted user behaviors is discussed further below with respect to FIG. 2.

The electronic device 102 may allow a user to select a behavioral policy that is intended to guide the user's behaviors, such as a dieting behavioral policy, that the user would like to adhere to. The electronic device 102 determines suggested behaviors for the user based at least on the behavioral policy. When providing context-aware behavioral feedback to the user, the electronic device 102 performs actions to facilitate the user with conforming predicted behaviors to the suggested behaviors determined from the behavioral policy. The electronic device 102 may collect data from the electronic sensor devices 106A-C, evaluate the collected data to characterize one or more behaviors as unhealthy, and provides context-aware behavioral feedback by attempting to modify the behaviors that are characterized as unhealthy, such as by facilitating the user with conforming the unhealthy behaviors to behaviors indicated by the dieting behavioral policy.

In one or more implementations, the electronic device 102 provides context-aware behavioral feedback to the user in the form of suggestions for improving monitored user behaviors, such as sleeping, eating, exercising, etc. For example, the electronic device 102 provides suggestions regarding the amount of time the user is sleeping, the amount of time the user is seated, the amount of exercising the user has done, such as walking, running, etc., the posture of the user, the amount of healthy foods, such fruits and/or vegetables, consumed by the user, the alertness of the user, etc. The electronic device 102 may download data, such as from the service provider server 110, for responding to recently sensed behaviors, such as playing relaxing music when the user is tired and/or has not slept enough, and/or playing an alarm when the user is tired but not in an environment for sleeping. The electronic device 102 provides context-aware behavioral feedback to the user for conforming the predicted behavior of the user to the suggested behavior of the user by adding subliminal visual frames, such as via the electronic sensor device 106B, to encourage and/or cause the user to dislike unhealthy foods, such as sweets or food in general, and like healthy foods, such as salads. Similar context-aware behavioral feedback provided by the electronic device 102 includes applying a filter to search engine results to identify and/or isolate healthy search results, such as color coding low fat restaurants on a map of search results, and/or removing other restaurants from the map of the search results.

The electronic device 102 may take into account what has been consumed by the user already in a given day and provides context-aware behavioral feedback to facilitate the user with maintaining a balanced calorie and/or vitamin intake for the day. For example, if the electronic device 102 determines that the user ate unhealthy food for breakfast, and that the user is hungry for lunch, the electronic device 102 provides healthy lunch suggestions to the user, and/or lunch suggestions that require substantial walking distance to counter additional calorie consumption. If the electronic device 102 determines that the user ate healthy food for breakfast, the electronic device 102 may reward the user with a broader selection of options for lunch and/or suggest options that include eating at home and/or driving. The electronic device 102 may monitor the amount and/or type of food already consumed by the user with facilitation of one or more of the electronic sensor devices 106A-C. For example, the electronic device 102 may request that the user identify their hand size, and the electronic device 102 uses the hand size to map a volume of food consumed, such as determined from a camera device of one or more of the electronic sensor devices 106A-C. The electronic device 102 can also identify the number of calories consumed by the user based at least on image matching, voice ordering recognition mapped to restaurant caloric content, box caloric label information (when cooking), etc.

In one or more implementations, the electronic device 102 provides context-aware behavioral feedback to the user in the form of a daily calorie meter and/or a balanced diet meter, such as via an output device of the electronic sensor device 106B. If the electronic device 102 detects that the user consumed a certain number of calories, then the electronic device 102 causes the meter to rise, and if the electronic device 102 determines that the user has exercised, then the electronic device 102 causes the meter to slowly fall, such as proportional to the number of calories that the user burned by exercising. The electronic device 102 may also provide a current weight, a goal weight, and/or information regarding long term behaviors, such as percentage of calories breaking the behavioral policy, and that such breaks have a cumulative total calories at some certain level of pounds. The electronic device 102 may perform a metabolism analysis of the user and/or the electronic device 102 provides a doctor interface to the user for doctor guidance and/or feedback via a portal. If the user is not exercising enough the electronic device 102 interfaces with a social networking engine to identify similarly situated other users and add them to the user's walking, running, etc., groups, such as to encourage the user to exercise more.

The electronic device 102 may determine a predicted and/or expected biometric profile for the user, based at least on an environmental profile associated with the user, such as an environmental profile that indicates that the user is driving a car. The electronic device 102 then obtains a current biometric profile for the user and determines whether the current biometric profile conforms to the predicted biometric profile. If the current biometric profile does not conform to the predicted biometric profile, the electronic device 102 provides context-aware behavioral feedback by performing an action to facilitate the user with conforming the current biometric profile to the predicted biometric profile. The action may be determined based at least on actions that have historically conformed the user's current biometric profile to the predicted biometric profile.

The electronic device 102 may attempt to associate behaviors and/or activities of the user with data received from one or more of the electronic sensor devices 106A-C, such as biometric data. Then, in view of unhealthy or bothersome biorhythmic indications, e.g. as indicated by the current biometric profile of the user, the electronic device 102 provides context-aware behavioral feedback by suggesting activities and/or behaviors (e.g. via advertising) that have previously proven successful for adjusting the current biometric profile of the user to conform to the predicted biometric profile.

The electronic device 102 may collect biometric profiles of a user and associated behaviors and/or environmental profiles to identify the effect that behaviors and/or activities have on the biometric profiles of the user, such as the effects of petting a dog, watching a boring or adventure movie, listening to a particular artist, eating a particular food, drinking coffee, talking to a particular person, etc. The behaviors and/or activities do not need to be specifically identified to determine the effect that they have on the biometric profile of the user. Thus, the electronic device 102 can provide context-aware behavioral feedback in the form of suggested behaviors and/or activities to coax the user away from some activities and thoughts, and toward others, such as to appropriately balance the current biometric profile of the user. Since users may differ, and a stimulus that makes one user happy may make another user angry, the performed actions and/or suggestions can be personalized for the particular user. An example process for performing actions to conform a current biometric profile of a user to an expected biometric profile is discussed further below with respect to FIG. 3. An example data flow of a system for performing actions to conform a current biometric profile of a user to an expected biometric profile is discussed further below with respect to FIG. 5.

The electronic device 102 may determine a predicted behavior of the user that is unsafe, such as based at least on a current environmental profile of the user, and the electronic device 102 provides context-aware behavioral feedback by attempting to correct the behavior before it is preformed and/or completed by the user. The electronic device 102 may identify dangerous environments, such as dangerous driving conditions, and provides context-aware behavioral feedback by performing an action when the biometric profile of the user does not conform to a predicted and/or expected biometric profile for the particular environment.

The electronic sensor device 106B may employ pattern and/or movement recognition to identify factory and/or home environments that are likely to result in injury, and provides an environmental profile indicating the same to the electronic device 102. The electronic device 102 may provide context-aware behavioral feedback by warning the user, and otherwise educates the user in an attempt at injury avoidance. Thus, the electronic device 102 uses context-awareness to identify dangerous environments, and provides context-aware behavioral feedback by alerting the user and/or attempting to modify the behavior of the user while in the dangerous environment.

The electronic device 102 may use geolocation information to determine dangerous environments, such as dangerous intersections where the user should be particularly alert, and/or weather information can be used to determine poor weather conditions when the user should be particularly alert. The electronic device 102 then provides context-aware behavioral feedback to alert the user to avoid hazards detected by the electronic device 102 and/or the electronic sensor devices 106A-C. In one or more implementations, the electronic sensor devices 106A-C determine when the user is likely to fall asleep, e.g. based at least on a current biometric profile of the user, recent sleep characteristics of the user, past sleep at the wheel events of the user, and/or and other susceptibilities. Thus, the electronic device 102 may predict that the user will fall asleep within a certain driving time on a certain type of road (highway), before the behavior actually occurs, and the electronic device 102 attempts to prevent and/or impede the predicted behavior from occurring. The electronic device 102 may also receive information from a vehicle of the user and/or one or more devices associated therewith, such as quick steering corrections and braking data currently and in the past. The electronic device 102 may use the information received from the vehicle to predict and/or measure a tired driving behavior of the user.

The electronic device 102 may perform one or more actions to provide context-aware behavioral feedback in response to detecting the expected sleeping at the wheel behavior, such as warn the user when a route is programmed, changing the route to one that requires more constant attention, selecting music for the user, suggesting a coffee shop stop, suggesting a motel, jolting the user, or otherwise waking up the user when the user is driving. The electronic device 102 may incorporate the amount of alcohol consumed by the user and/or medications taken by the user when predicting the sleep behavior. In one or more implementations, bad driving behaviors by the user (predicted behaviors and/or current behaviors that are beyond the norm for the user and/or outside of a safety level), in addition to a current biometric profile, recent user activity history, and/or long term related history, can be used to force the user to pull over and/or to prevent the user's vehicle from driving. The electronic device 102 may gather data regarding sleep patterns of the user generally, and/or associated biometric profile information of the user, and the electronic device 102 compares how the user (and/or other users) performed various activities under similar sleep patterns and/or biometric profiles, such as from a safety standpoint. An example process of conforming a user's biometric profile to a safe biometric profile for a given environment is discussed further below with respect to FIG. 3.

The electronic device 102 may use the current biometric profile of the user to provide context-aware behavioral feedback with respect to online behaviors of the user, such as online searching. The electronic device 102 may implement context-aware behavioral feedback to online searching by using the current biometric profile of the user as input to a search or selection algorithm. For example, the current biometric profile of the user and/or an associated environmental profile can be used as a search input, and/or to supplement or modify search input. In one or more implementations, the biometric profile of the user indicates a relaxed state and prone position of the user, the environmental profile indicates that the user is at home late in the day on Saturday, and as a result the electronic device 102 initiates playing music having an upbeat tempo, such as to encourage the user to exercise. If the environmental profile indicates that it is night time, the electronic device 102 initiates the playing of soothing music, and/or initiates stopping the music when the current biometric profile of the user indicates that the user is falling asleep.

The electronic device 102 may receive a search from the user for music by a particular band, and the electronic device 102 considers the current biometric profile and/or a current environmental profile of the user, to provide context-aware behavioral feedback by ranking songs by the band in different orders. For example, the songs that have historically proven (by the user and/or by others similar users) to cause surges in biometric profiles might be offered higher on the search results list in the morning than late at night on a work day. The supplemented searching may be applied to any systems that include a search and/or user preference feature, such as any Internet search platforms. An example data flow of a system for providing context-aware behavioral feedback through biometric profile and/or environmental profile supplemented searching is discussed further below with respect to FIG. 6.

In one or more implementations, the network environment 100 may include additional users, such as houseguests, co-workers, etc., and at least one of the additional users may be associated with at least one additional electronic sensor device 106A-C and/or at least one electronic device 102. The electronic device 102 of the user may receive current biometric profiles of the additional users, expected/predicted biometric profiles of the additional users, and/or preferences of the additional users, such as musical preferences, food preferences, etc., via the electronic sensor devices and/or electronic devices of the additional users. The preferences of the additional users may be default preferences and/or predicted preferences. The electronic device 102 may provide the preferences and/or profiles for display to the user, such as via a screen of the electronic device 102 and/or via an output device associated with the electronic sensor device 106B. The preferences may not be provided for display to the additional users.

The preferences may be genres, such as spicy food, or classical music, and/or the preferences may be specific items, such as specific foods one of the additional users likes and/or has eaten in the past month, or a music playlist of one of the additional users. The user of the electronic device 102 views the preferences of the additional users, and makes selections accordingly. The preferences may include negative preferences, such as dislikes and/or foods that an additional user is allergic to. The electronic device 102 may provide the preferences of all of the additional users for display and/or selection, and/or the electronic device 102 may filter the preferences to only display group consensus items as possible selections, such as for music.

In one or more implementations, the electronic device 102 provides context-aware behavioral feedback for the users collectively by automatically making selections and/or controlling one or more of the electronic devices 112A-C, based at least on the received preferences, current biometric profiles, predicted biometric profiles and/or other data received from the devices of the additional users. The electronic device 102 may predict preferences of the additional users based at least on the current and/or predicted biometric profiles of the additional users, such as by sensing activities, moods, biometric profiles, etc. of the additional users. The electronic device 102 may receive other information from the electronic devices associated with the additional users that the electronic devices determines to be useful. For example, recent re-listening to a particular song by an additional user results in a preference for such song being provided to the electronic device 102, such as for consideration in selecting to trigger background music and playing the song.

The electronic device 102 may also receive immediate context-aware behavioral feedback from the electronic devices and/or electronic sensor devices of the additional users that indicates whether the additional users are enjoying a current selection, such as a current music selection, and the electronic device 102 adjusts the music selection in real time based at least on the feedback. The electronic device 102 may receive updated current biometric profiles of the additional users that the electronic device 102 compares to previously received biometric profiles of the additional users to determine the effect of the current selection on the additional users. Thus, the electronic device 102 may receive non-verbal feedback that is used to impact the selections made by the user and/or the electronic device 102.

In one or more implementations, the electronic device 102 gathers and store time-related data that includes bio-sensing data, such as biometric data, user interaction data, and/or software application data. The electronic device 102 may process the time-related data to identify bio-impacting relationships, such as between the bio-sensing data and the user interaction data and/or software application data. The electronic device 102 may identify current biometric data of a user, such as from the gathered bio-sensing data, and the electronic device 102 responds to the identification by performing an action that attempts to alter future bio-sensing data of the user.

In one or more implementations, the electronic device 102 stores first data with a timing relationship. The first data may include bio-sensing related data and/or software application related data that is gathered over a period of time. The electronic device 102 processes the first data to identify software application related data that has a bio-impact, such as software application related data that impacts the bio-sensing related data. The electronic device 102 performs an action to a cause a future generation of the software application related data to cause the first bio-impact, such as in order to facilitate conforming a current biometric profile of the user to an expected biometric profile of the user.

In one or more implementations, the electronic device 102 may store gathered data with a timing relationship. The gathered data may include bio-sensing related data and device operational data that is collected over time. The electronic device 102 processes the gathered data to identify a predictive association between a first portion of the bio-sensing related data, first portion of the device operational data, and/or non-bio-sensing context information. The electronic device 102 performs an action to cause a future generation of the device operational data in response to obtaining future counterparts of the first portion of the bio-sensing related data. The action includes sending a communication to one or more remote devices, providing an offer to a user, performing a software reconfiguration, and/or performing a software selection. The gathered data may originate from within the electronic device 102 and/or from one or more environmental devices.

Figure 2:
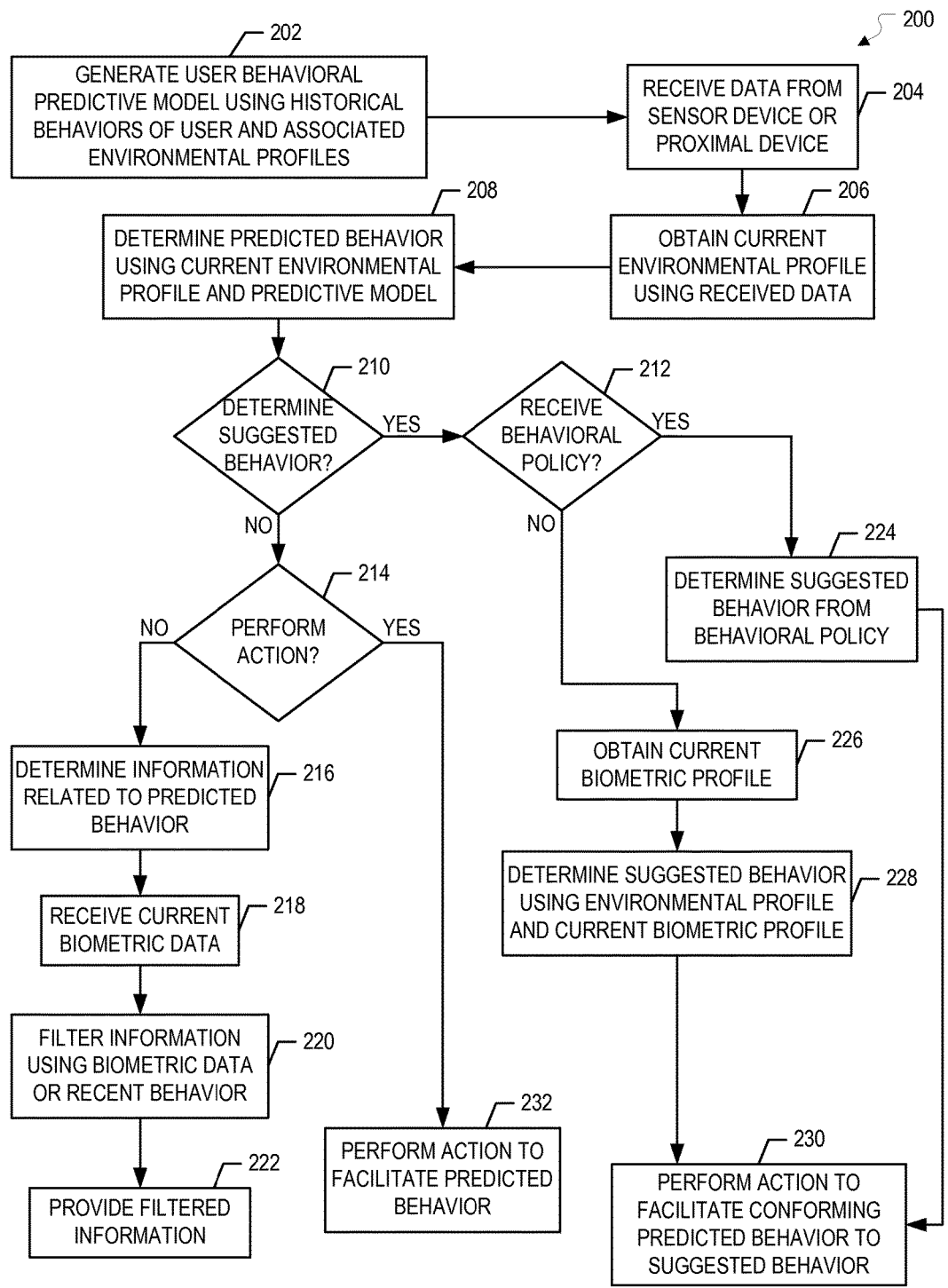
FIG. 2 illustrates a flow diagram of an example process of a context-aware decision making system in accordance with one or more implementations.

FIG. 2 illustrates a flow diagram of an example process 200 of a context-aware decision making system in accordance with one or more implementations. For explanatory purposes, the example process 200 is primarily described herein with reference to electronic device 102 of FIG. 1; however, the example process 200 is not limited to the electronic device 102 of FIG. 1, and the example process 200 may be performed by one or more components of the electronic device 102. In one or more implementations, all or part of the example process 200 may be performed by the service provider server 110, by one or more of the electronic sensor devices 106A-C, and/or by the electronic device 102. Further for explanatory purposes, the blocks of the example process 200 are described herein as occurring in serial, or linearly. However, multiple blocks of the example process 200 may occur in parallel. In addition, the blocks of the example process 200 may be performed a different order than the order shown and/or one or more of the blocks of the example process 200 may not be performed.

The electronic device 102 may implement the example process 200 to generate a user behavioral predictive model to predict a behavior of a user in a current environment and then provide context-aware behavioral feedback to the user by providing information related to the predicted behavior of the user, performing an action to facilitate the predicted behavior of the user, and/or performing an action to facilitate conforming the predicted behavior of the user to a suggested behavior, such as a suggested behavior determined from a behavioral policy.

The electronic device 102 generates the user behavioral predictive model based at least in part on historical behaviors of the user and/or associated environmental profiles of the user at the time that the historical behaviors were performed (202). In one or more implementations, the electronic device 102 performs one or more feature selection algorithms to determine one or more environmental variables of the environmental profiles to use as features for the predictive model, such as the environmental variables that are most indicative of the corresponding historical behaviors. The electronic device 102 may use an algorithm, such as a k-nearest neighbor algorithm, to generate the predictive model using at least the determined features and the associated historical behaviors. The electronic device 102 may receive the user behavioral predictive model, e.g. from the service provider server 110. The electronic device 102 may continuously retrain, or adjust, the user behavioral predictive model as additional behaviors of the user are observed.

The electronic device 102 receives data from one or more of the electronic sensor devices 106A-B, and/or from the electronic devices 112A-C, from which the current environment of the user is obtainable and/or detectable (204). The electronic device 102 may receive the data from a sensor of the electronic device 102, such as a positioning sensor, an accelerometer, etc. The electronic device 102 obtains and/or detects the current environmental profile of using at least the received data (206). For example, the current environmental profile may indicate that the user is at their home, standing in their kitchen, looking in their refrigerator on a Sunday morning.

The electronic device 102 determines a predicted behavior of the user by applying the current environmental profile to the user behavioral predictive model (208). For example, the electronic device 102 determines a predicted behavior of eating breakfast. The electronic device 102 determines whether a suggested behavior can be determined (210). For example, the electronic device 102 determines whether a behavioral policy was received for the user (212). The behavioral policy indicates behaviors suggested for the user to maintain an associated lifestyle, such as a diet behavioral policy.

If a behavioral policy was received for the user (212), the electronic device 102 determines a suggested behavior based at least on the behavioral policy (224). In one or more implementations, the suggested behavior is determined based at least on the behavioral policy and recent behaviors of the user. For example, the behavioral policy allows the user to consume a total number of calories per day and the suggested behavior is based at least on the number of calories the user has already consumed for the day relative to the total number of calories allowed. The electronic device 102 then performs an action to facilitate conforming the predicted behavior to the suggested behavior (230). For example, the electronic device 102 suggests that the user not prepare a meal or eat any foods if the user has recently consumed a large number of calories, or that the user eat a higher calorie meal if the user has not consumed many calories that day.

If the electronic device 102 did not receive a behavioral policy for the user (212), the electronic device 102 obtains the current biometric profile of the user (226). For example, the electronic device 102 receives one or more biometric data items from the electronic sensor devices 106A-C, and determines the biometric profile of the user based at least in part on the received biometric data items. The electronic device 102 then determines the suggested behavior for the user based at least in part on the current environmental profile and the current biometric profile of the user (228). For example, the electronic device 102 applies the current biometric profile of the user and/or the current environmental profile to another predictive model that indicates the behaviors and/or activities that other users have found preferable in the past when the other users had similar biometric profiles as the current biometric profile of the user and/or when the other users (such as healthy users) were in a similar environment as the environment described by the current environmental profile of the user. The another predictive model may be provided by, for example, a doctor, a dietary expert, a governmental agency, such as the FDA, or the like. The electronic device 102 then performs an action to facilitate conforming the predicted behavior of the user to the suggested behavior (230).

If the electronic device 102 determines that a suggested behavior cannot be determined (210), the electronic device 102 determines whether an action can be performed that facilitates the predicted behavior (214). For example, the electronic device 102 determines whether it can perform an action that facilitates the predicted behavior and/or whether the electronic device 102 can instruct any other electronic devices 112A-C to perform an action that facilitates the predicted behavior. If the electronic device 102 determines that an action can be performed that facilitates the predicted behavior (214), the electronic device 102 performs the action to facilitate the predicted behavior (232). For example, if the electronic device 102 predicts that the user will prepare a meal that requires an oven device to be pre-heated to a particular temperature, the electronic device 102 initiates preheating the oven device to the particular temperature, such as by transmitting an instruction to the oven device.

If the electronic device 102 determines that there are no actions that can be performed to facilitate the predicted behavior (214), the electronic device 102 determines and/or retrieve information related to the predicted behavior (216). For example, the electronic device 102 retrieves information regarding foods that are available in a refrigerator device. The electronic device 102 then receives current biometric data of the user, such as from one or more of the electronic sensor devices 106A-C (218).

The electronic device 102 filters the information based at least on the current biometric data of the user and/or recent behaviors of the user (220). For example, if the biometric data of the user indicates that the user is thirsty, and/or the recent behavior of the user indicates that the user was exercising, the electronic device 102 filters the information to only include information regarding sports drinks that are available in the refrigerator. The electronic device 102 then provides the filtered information to the user (222), such as via a display, via the electronic sensor device 106B, and/or via an output of the refrigerator device. In one or more implementations, the electronic device 102 provides the information to the user (222) without filtering the information. The electronic device 102 may provide information related to a predicted behavior (222), in addition to performing an action that facilitates the predicted behavior (232).

Figure 3:
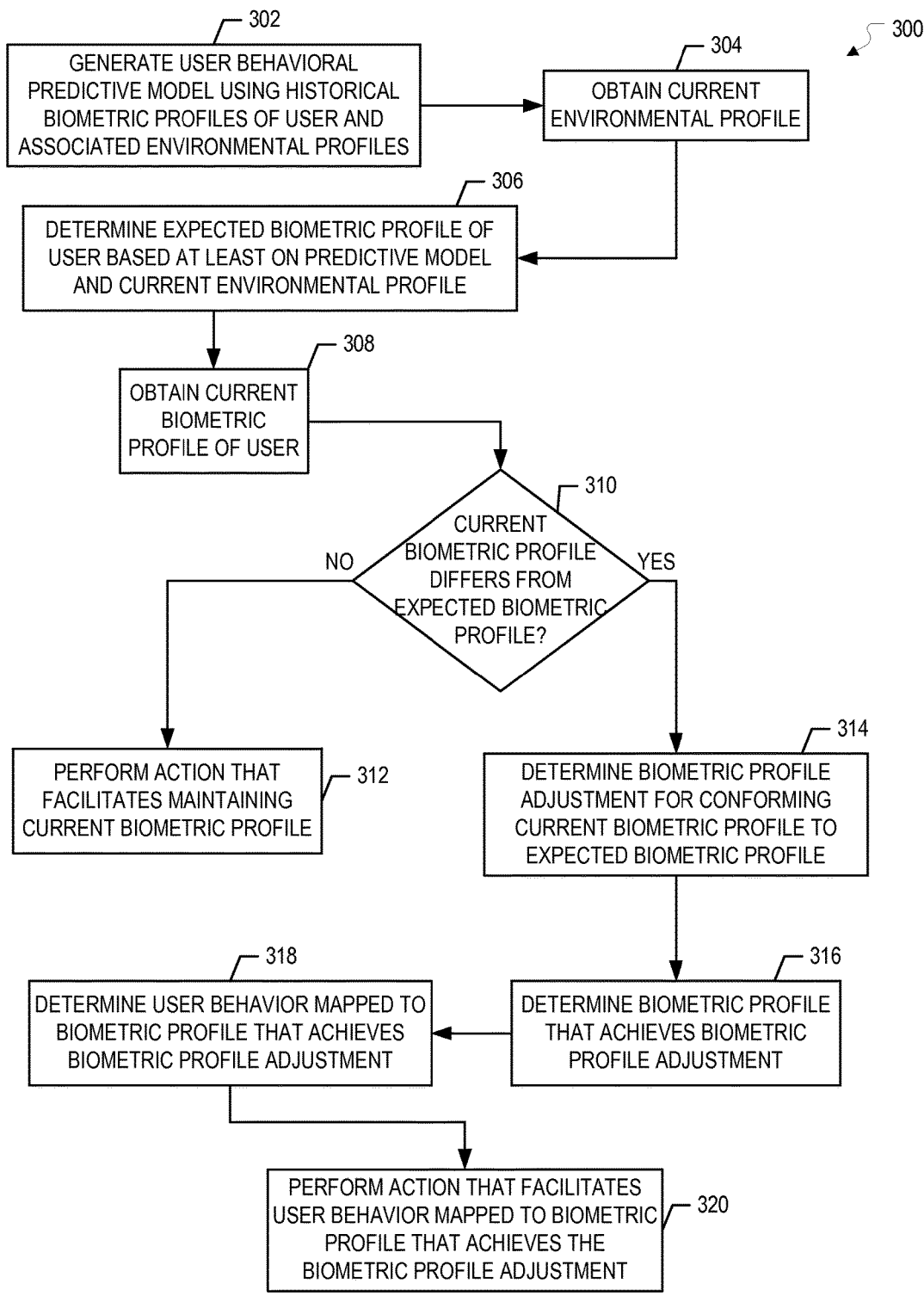
FIG. 3 illustrates a flow diagram of an example process of a context-aware decision making system in accordance with one or more implementations.

FIG. 3 illustrates a flow diagram of an example process 300 of a context-aware decision making system in accordance with one or more implementations. For explanatory purposes, the example process 300 is primarily described herein with reference to electronic device 102 of FIG. 1; however, the example process 300 is not limited to the electronic device 102 of FIG. 1, and the example process 300 may be performed by one or more components of the electronic device 102. In one or more implementations, all or part of the example process 300 may be performed by the service provider server 110, by one or more of the electronic sensor devices 106A-C, and/or by the electronic device 102. Further for explanatory purposes, the blocks of the example process 300 are described herein as occurring in serial, or linearly. However, multiple blocks of the example process 300 may occur in parallel. In addition, the blocks of the example process 300 may be performed a different order than the order shown and/or one or more of the blocks of the example process 300 may not be performed.

In one or more implementations, the electronic device 102 implements the example process 300 to generate a user behavioral predictive model to determine an expected biometric profile of the user in a current environment and then provide context-aware behavioral feedback to the user by performing an action that facilitates the user with maintaining their current biometric profile (when their current biometric profile substantially coincides with the expected biometric profile of the user for the current environment) or that facilitates the user with conforming their current biometric profile to the expected biometric profile of the user for the current environment.

The electronic device 102 generates the user behavioral predictive model based at least in part on historical biometric profiles of the user and/or associated environmental profiles at the time that the historical biometric profiles were collected (302). The user behavioral predictive model may be based at least on the historical biometric profiles of other users and the associated environmental profiles of the other users. The user behavioral predictive model may be based at least on recommended biometric profiles for users for given environmental profiles, such as the biometric profiles indicated by a manufacturer of a vehicle, and/or biometric profiles set by a regulating and/or governmental agency.

The electronic device 102 obtains a current environmental profile that indicates a current environment of the user, such as based at least on data received from one or more of the electronic sensor devices 106A-B and/or from one or more of the electronic devices 112A-C (304). The electronic device 102 determines an expected biometric profile of the user based at least on the user behavior predictive model and/or the current environmental profile (306). For example, the electronic device 102 applies the current environmental profile of the user to the user behavioral predictive model to determine an expected biometric profile of the user (308). The expected biometric profile may indicate the typical biometric profile of the user for the environment, a recommended biometric profile of the user for the environment, and/or a minimum biometric profile of the user for the environment, such as indicated by a governmental agency. For example, if the environmental profile indicates that the user is driving in an identified type of car, on an identified road, at an identified time of day, and in identified weather and/or traffic conditions, the expected biometric profile may indicate the minimum biometric profile for operating the identified type of car on the identified road at the identified time of day and in the identified weather and/or traffic conditions. If the expected biometric profile is not based at least on the typical biometric profile of the user, the expected biometric profile may be adjusted based at least on the typical biometric profile of the user, such as to account for biometric particularities of the user.

The electronic device 102 determines whether the current biometric profile of the user differs from the expected biometric profile for the user (310), such as by more than a threshold amount. If the current biometric profile does not differ from the expected biometric profile (310), such as by more than the threshold amount, the electronic device 102 performs an action that facilitates maintaining the current biometric profile of the user (312). For example, the electronic device 102 selects a next music track and/or station that is similar, e.g. consistent tempo, etc., with music currently being listened to by the user.

If the electronic device 102 determines that the current biometric profile of the user differs from the expected biometric profile of the user (310), such as by more than the threshold amount, the electronic device 102 determines a biometric profile adjustment for conforming the current biometric profile to the expected biometric profile (314). For example, if the current biometric profile of the user indicates that the heart rate of the user is below the expected heart rate for the user for the current environment, the biometric profile adjustment indicates that the heart rate of the user should be elevated to a level consistent with the expected biometric profile.

The electronic device 102 determines a biometric profile of the user that achieves the biometric profile adjustment (316). For example, if the heart rate of the user needs to be elevated to a particular level, the electronic device 102 identifies a biometric profile for which the heart rate of the user is at or above the particular level. The electronic device 102 determines a user behavior that is mapped to the biometric profile that achieves the biometric profile adjustment (318). For example, the electronic device 102 identifies historical user behaviors that are mapped to the biometric profile, such as certain musical selections that have previously achieved the biometric profile, and/or the electronic device 102 utilizes a predictive model to identify behaviors that are associated with the biometric profile. The electronic device 102 then performs an action that facilitates the user behavior that is mapped to the biometric profile that achieves the biometric profile adjustment (320).

Figure 4:
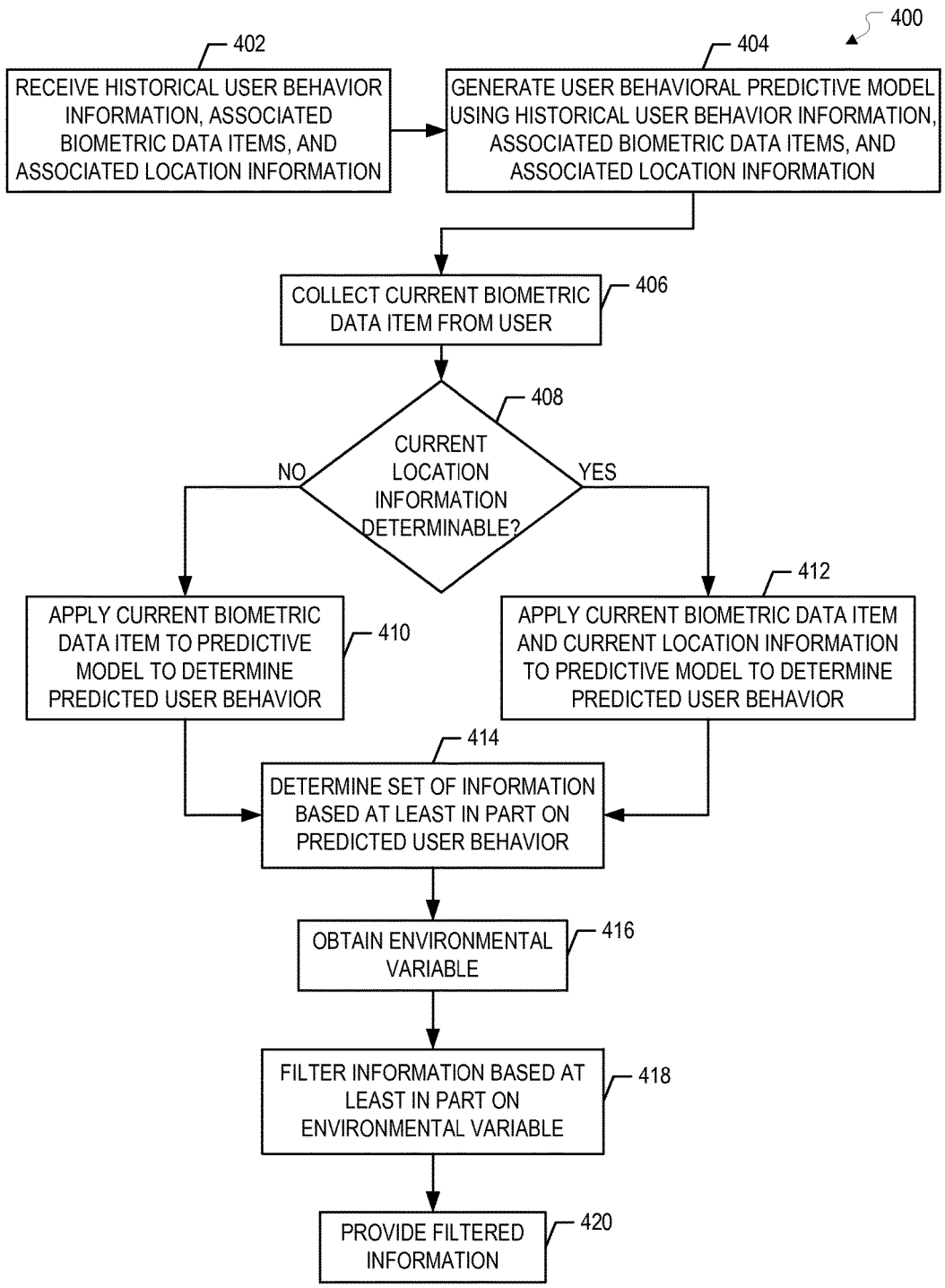
FIG. 4 illustrates a flow diagram of an example process of a context-aware decision making system in accordance with one or more implementations.

FIG. 4 illustrates a flow diagram of an example process 400 of a context-aware decision making system in accordance with one or more implementations. For explanatory purposes, the example process 400 is primarily described herein with reference to electronic device 102 of FIG. 1; however, the example process 400 is not limited to the electronic device 102 of FIG. 1, and the example process 400 may be performed by one or more components of the electronic device 102. In one or more implementations, all or part of the example process 400 may be performed by the service provider server 110, by one or more of the electronic sensor devices 106A-C, and/or by the electronic device 102. Further for explanatory purposes, the blocks of the example process 400 are described herein as occurring in serial, or linearly. However, multiple blocks of the example process 400 may occur in parallel. In addition, the blocks of the example process 400 may be performed a different order than the order shown and/or one or more of the blocks of the example process 400 may not be performed.

In one or more implementations, the electronic device 102 implements the example process 400 to generate a user behavioral predictive model to predict a behavior of a user based on the location and/or current biometric profile of the user, and then provide context-aware behavioral feedback to the user by providing information related to the predicted behavior of the user where the information is filtered based at least on a current environment of the user.

The electronic device 102 receives historical user behavior information that describes historical user behaviors, and associated biometric data items and location information that were collected at or near the time that the historical behaviors were performed (402). The electronic device 102 generates a user behavioral predictive model using at least the historical user behavior information, the associated biometric data items and the associated location information (404). The electronic device 102 collects current biometric data items from the user, such as via the electronic sensor devices 106A-C (406). The electronic device 102 determines whether current location information associated with the user is determinable (408), such as from data received from one or more of the electronic sensor devices 106A-C.

If the current location information associated with the user is determinable (408), the electronic device 102 applies the current biometric data and current location information to the predictive model to determine a predicted user behavior (412). If the current location information associated with the user cannot be determined (408), the electronic device 102 applies the current biometric data to the predictive model (without any location information) to determine a predicted user behavior (410).

The electronic device 102 determines a set of information based at least in part on the predicted user behavior (414). For example, if the predicted behavior is that the user will listen to music, the electronic device 102 determines the songs that are available for the user to listen to. The electronic device 102 obtains at least one environmental variable, such as time of day, recent user behaviors, etc. (416). The electronic device 102 filters the information based at least in part on the environmental variable (418). For example, the electronic device 102 filters songs that the user recently listened to and/or the electronic device 102 filters songs based at least on the time of day. The electronic device 102 then provides the filtered information to the user, such as via a screen on the electronic device 102 and/or via an output device of another device, such as the electronic sensor device 106B (420).

Figure 5:
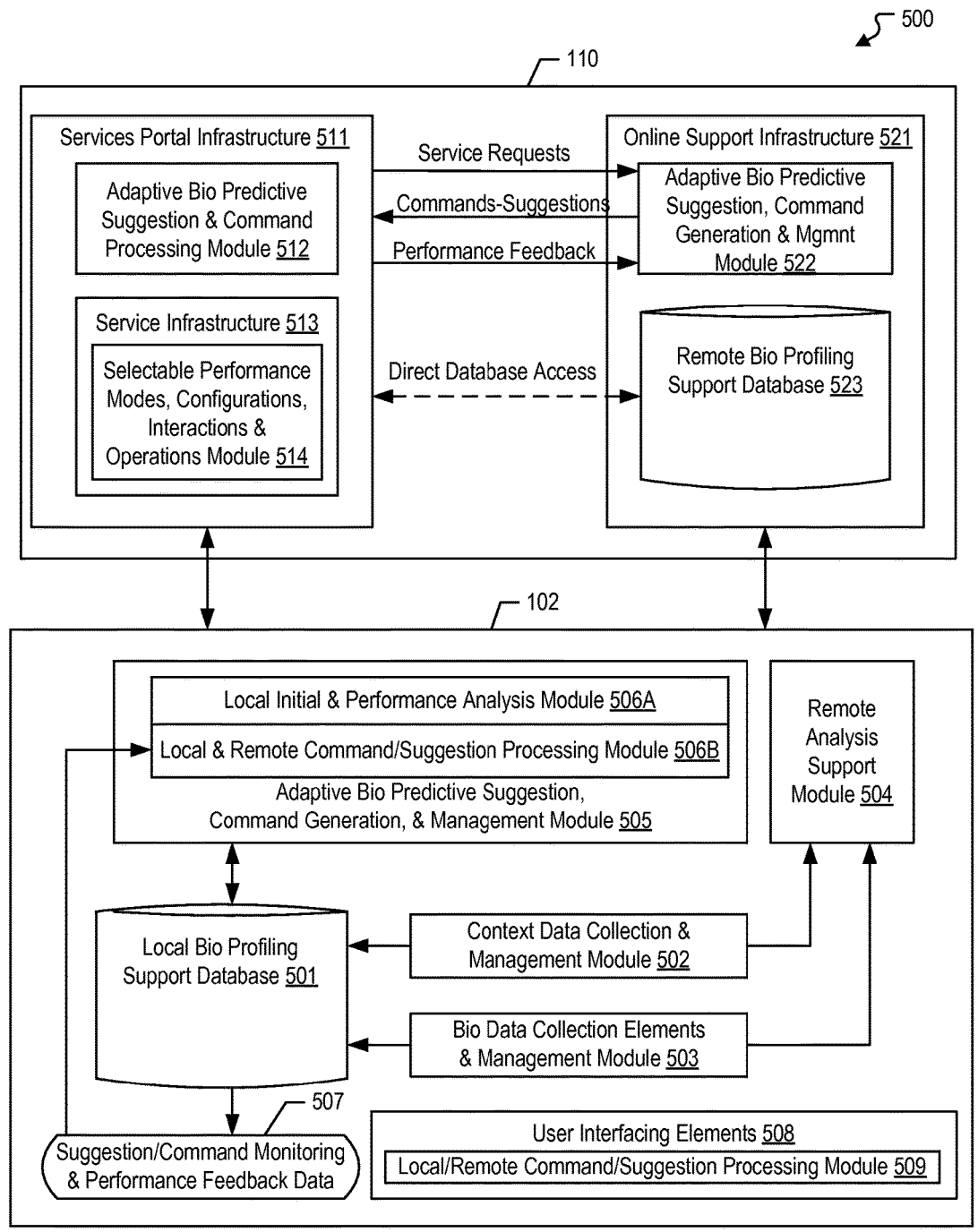
FIG. 5 illustrates an example data flow of a context-aware decision making system in accordance with one or more implementations.

FIG. 5 illustrates an example data flow 500 of a context-aware decision making system in accordance with one or more implementations. Not all of the depicted components may be used, however, and one or more implementations may include additional components not shown in the figure. Variations in the arrangement and type of the components may be made without departing from the spirit or scope of the claims as set forth herein. Additional components, different components, or fewer components may be provided.

The data flow 500 includes data and communications that may be transmitted between the electronic device 102 and the service provider server 110 to provide context aware behavioral feedback to a user. The data flow 500 further illustrates components of the electronic device 102 and the service provider server 110 that facilitate providing the context-aware behavioral feedback to the user.

In this regard, the electronic device 102 includes a context data collection and management module 502, a biometric data collection elements and management module 503, a remote analysis support module 504, user interfacing elements 508, an adaptive biometric predictive suggestion, command generation, and management module 505, and a local biometric profiling support database 501. The adaptive biometric predictive suggestion, command generation, and management module 505 includes a local initial and performance analysis module 506A, and a local and remote command/suggestion processing module 506B. The user interfacing elements 508 may include one or more applications, operating systems, and/or browsers, and may also include a local/remote command/suggestion processing module 509. The local biometric profiling support database 501 may store local current and historical biometric information, local current and historical context information, such as environmental profiles, and/or related analysis information. The local biometric profiling support database 501 provides suggestion/command monitoring and performance feedback data 507 to the adaptive biometric predictive suggestion, command generation, and management module 505.

The service provider server 110 includes a services portal infrastructure 511 and an online support infrastructure 521. The services portal infrastructure 511 includes an adaptive biometric predictive suggestion and command processing module 512, and a services infrastructure 513. The services infrastructure 513 includes a selectable performance modes, configurations, interactions, and operations module 514. The online support infrastructure 521 includes an adaptive biometric predictive suggestion, command generation, and management module 522, and a remote biometric profiling support database 523. The remote biometric profiling support database 523 may store local current and historical biometric data, local current and historical context information, such as environmental profiles, and/or related analysis information.

In the data flow 500, the electronic device 102 collects biometric data items, such as from the electronic sensor devices 106A-C, via the biometric data collection elements & management module 503. The electronic device 102 collects environmental variables and/or environmental profiles via the context data collection and management module 502. The electronic device 102 may store the biometric data items and/or environmental variables in the local biometric profiling support database 501. The adaptive biometric predictive suggestion, command generation, and management module 505 then retrieves the stored biometric data items and/or environmental variables from the local biometric profiling support database 501, and generates one or more commands and/or suggestions based at least in part on the retrieved biometric data items and/or environmental variables. The suggestions and/or commands may be provided to a user via the user interfacing elements 508. The electronic device 102 may monitor the provided suggestions, commands, and/or any associated feedback, and provide the suggestion/command monitoring and performance feedback data 507 to the adaptive biometric predictive suggestion, command generation, and management module 505. The adaptive biometric predictive suggestion, command generation, and management module 505 adjusts the provided suggestions and/or commands based at least on the suggestion/command monitoring and performance feedback data 507.

The electronic device 102 may provide the biometric data items, the environmental variables, and/or the suggestion/command monitoring and performance feedback data 507 to the remote analysis support module 504. The remote analysis support module 504 may provide the biometric data items, the environmental variables, and/or the suggestion/command monitoring and performance feedback data 507 to the service provider server 110, such as for storage in the remote biometric profiling support database 523. The services portal infrastructure 511 of the service provider server 110 may receive service requests, such as from the electronic device 102, and forwards the service requests to the adaptive biometric predictive suggestion, command generation, and management module 522. The adaptive biometric predictive suggestion, command generation, and management module 522 provides commands-suggestions to the services portal infrastructure 511. The services portal infrastructure 511 forwards the commands-suggestions to the electronic device 102.

Figure 6:
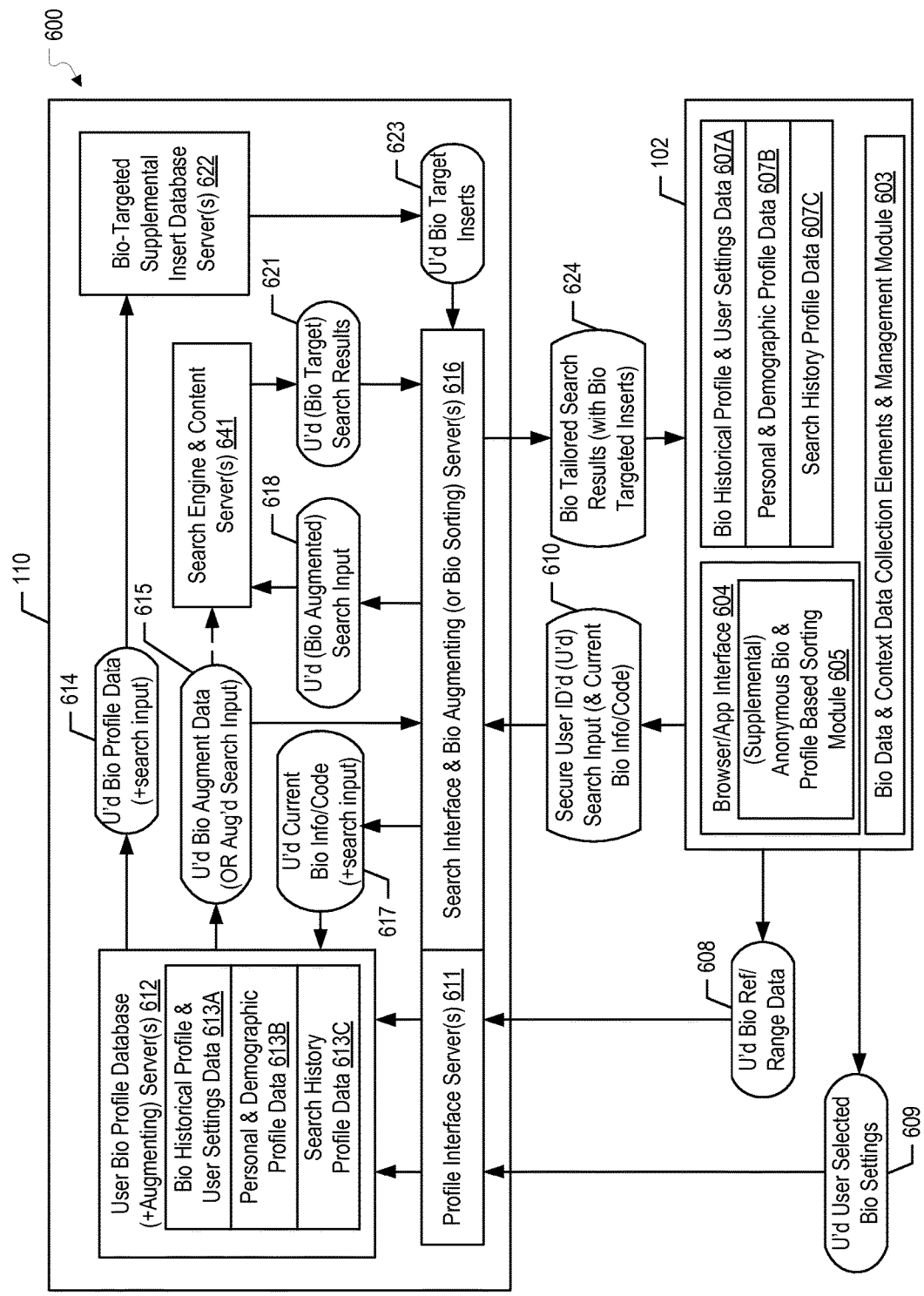
FIG. 6 illustrates an example data flow of a context-aware decision making system in accordance with one or more implementations.

FIG. 6 illustrates an example data flow 600 of a context-aware decision making system in accordance with one or more implementations. Not all of the depicted components may be used, however, and one or more implementations may include additional components not shown in the figure. Variations in the arrangement and type of the components may be made without departing from the spirit or scope of the claims as set forth herein. Additional components, different components, or fewer components may be provided.

The data flow 600 includes data and communications that may be transmitted between the electronic device 102 and the service provider server 110 to provide context aware behavioral feedback with respect to online behaviors of a user, such as online searching. The data flow 600 further illustrates components of the electronic device 102 and the service provider server 110 that facilitate providing context-aware behavioral feedback with respect to the online behaviors of the user.

In this regard, the electronic device 102 includes a browser/application interface 604, a biometric data and context data collection elements and management module 603, and a memory that stores biometric historical profile and user settings data 607A, personal and demographic profile data 607B, and search history profile data 607C. The browser/application interface 604 includes a supplemental anonymous biometric and profile based sorting module 605.

As previously discussed with respect to FIG. 1, the service provider server 110 may include multiple computing devices and/or server devices. With respect to the data flow 600, the service provider server 110 includes one or more profile interfaces servers 611, one or more user biometric profile database servers 612, one or more search interface and biometric augmenting servers 616, one or more search engine and content servers 641, and one or more biometric targeted supplemental insert database servers 622. The one or more user biometric profile database servers 612 store biometric historical profile and user settings data 613A, personal and demographic profile data 613B, and/or search history profile data 613C.

In the data flow 600, the electronic device 102 locally stores, such as in a secure element, one or more of the biometric historical profile and user settings data 607A, the personal and demographic profile data 607B, and/or the search history profile data 607C. The electronic device 102 receives search input, such as via the browser/application interface 604, and provides the search input, a secure user identifier, and/or a current biometric information/code 610 to the service provider server 110, such as to the one or more search interface and biometric augmenting servers 616. In one or more implementations, the current biometric information/code is indicative of the current biometric profile of the user. The one or more search interface and biometric augmenting servers 616 provide the user identified current biometric information/code and/or search input 617 to the one or more user biometric profile database servers 612.

The one or more user biometric profile database servers 612 determine user identified biometric augmented data and/or augmented search input 615 and provide the user identified biometric augmented data and/or augmented search input 615 to the one or more search interface and biometric augmenting servers 616. The user identified biometric augmented data and/or augmented search input 615 may be provided directly to the one or more search engine and content servers 641. The one or more search interface and biometric augmenting servers 616 use the user identified biometric augmented data and/or augmented search input 615 to generate and provide user identified biometric augmented search input 618 to the one or more search engine and content servers 641. The one or more search engine and content servers 641 use the user identified biometric augmented search input 618 and/or user identified biometric augmented data and/or augmented search input 615 to generate and provide user identified biometric targeted search results 621 back to the one or more search interface and biometric augmenting servers 616.

The one or more user biometric profile database servers 612 may provide user identified biometric profile data and search input 614 to the one or more biometric targeted supplemental insert database servers 622. The one or more biometric targeted supplemental insert database servers 622 use the user identified biometric profile data and search input 614 to generate and provide user identified biometric targeted inserts 623, such as advertisements, to the one or more search interface and biometric augmenting servers 616. The one or more search interface and biometric augmenting servers 616 use the user identified biometric targeted search results 621 and/or the user identified biometric targeted inserts 623 to generate, sort, and/or provide biometric tailored search results with biometric targeted inserts 624 to the electronic device 102. The electronic device 102 provides the biometric tailored search results with biometric targeted inserts 624 to a user, such as via the browser/application interface 604.

The electronic device 102 may communicate user identified user selected biometric settings 609 to the service provider server 110, such as to the one or more profile interface servers 611. The one or more profile interface servers 611 stores the user identified user selected biometric settings 609 in the one or more user biometric profile database servers 612. The electronic device 102 may communicate user identified biometric reference/range data 608 to the service provider server 110, such as to the one or more profile interface servers 611. The one or more profile interface servers 611 stores the user identified biometric reference/range data 608 in the one or more user biometric profile database servers 612.

Figure 7:
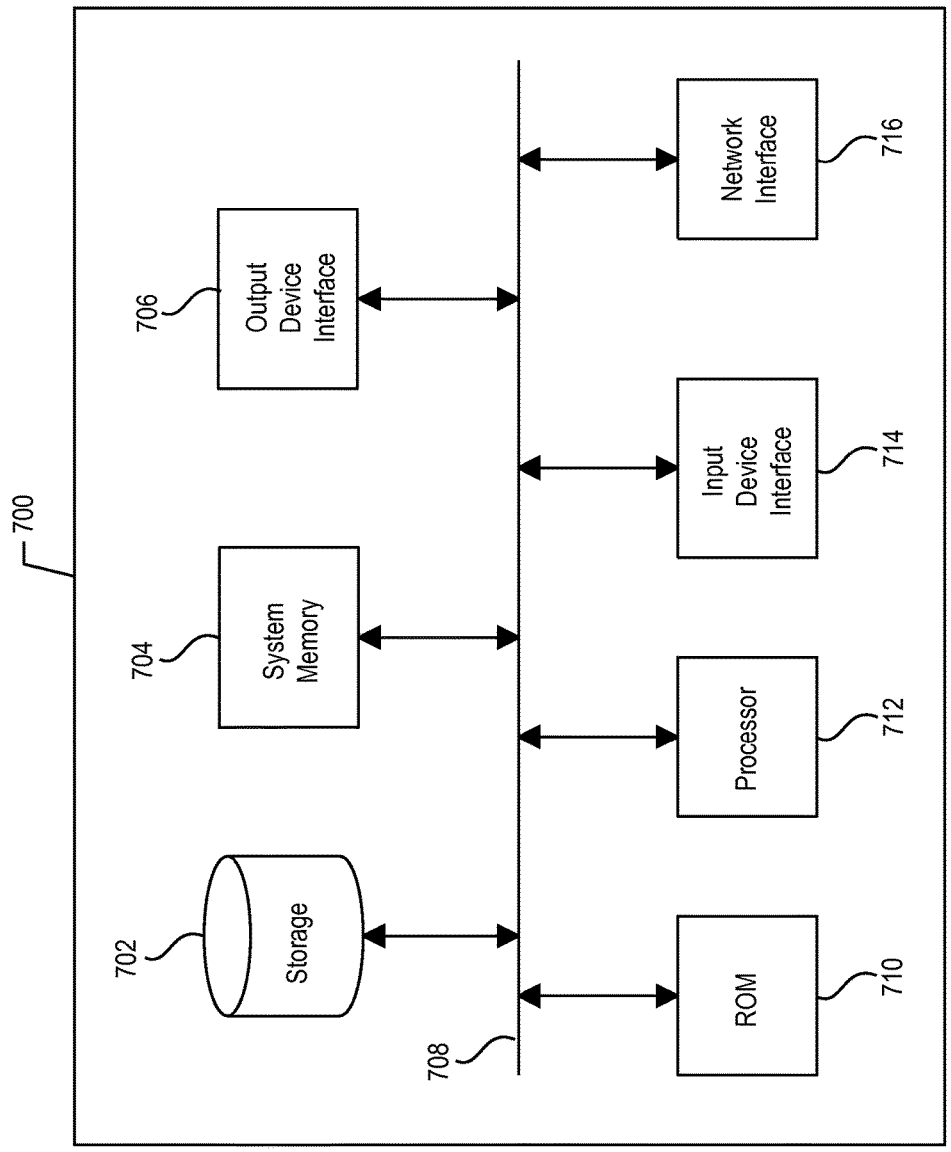
FIG. 7 conceptually illustrates an example electronic system with which one or more implementations of the subject technology can be implemented.

FIG. 7 conceptually illustrates an example electronic system 700 with which one or more implementations of the subject technology can be implemented. The electronic system 700, for example, may be, or may include, the electronic device 102, one or more of the electronic sensor devices 106A-C, the service provider server 110, one or more of the electronic devices 112A-C, a desktop computer, a laptop computer, a tablet computer, a phone, and/or generally any electronic device. Such an electronic system 700 includes various types of computer readable media and interfaces for various other types of computer readable media. The electronic system 700 includes a bus 708, one or more processing unit(s) 712, a system memory 704, a read-only memory (ROM) 710, a permanent storage device 702, an input device interface 714, an output device interface 706, one or more network interface(s) 716, and/or subsets and variations thereof.

The bus 708 collectively represents all system, peripheral, and chipset buses that communicatively connect the numerous internal devices of the electronic system 700. In one or more implementations, the bus 708 communicatively connects the one or more processing unit(s) 712 with the ROM 710, the system memory 704, and the permanent storage device 702. From these various memory units, the one or more processing unit(s) 712 retrieves instructions to execute and data to process in order to execute the processes of the subject disclosure. The one or more processing unit(s) 712 can be a single processor or a multi-core processor in different implementations.

The ROM 710 stores static data and instructions that are utilized by the one or more processing unit(s) 712 and other modules of the electronic system 700. The permanent storage device 702, on the other hand, may be a read-and-write memory device. The permanent storage device 702 may be a non-volatile memory unit that stores instructions and data even when the electronic system 700 is off. In one or more implementations, a mass-storage device (such as a magnetic or optical disk and its corresponding disk drive) may be used as the permanent storage device 702.

In one or more implementations, a removable storage device (such as a floppy disk, flash drive, and its corresponding disk drive) may be used as the permanent storage device 702. Like the permanent storage device 702, the system memory 704 may be a read-and-write memory device. However, unlike the permanent storage device 702, the system memory 704 may be a volatile read-and-write memory, such as random access memory (RAM). The system memory 704 may store one or more of the instructions and/or data that the one or more processing unit(s) 712 may utilize at runtime. The processes of the subject disclosure may be stored in the system memory 704, the permanent storage device 702, and/or the ROM 710. From these various memory units, the one or more processing unit(s) 712 retrieve instructions to execute and data to process in order to execute the processes of one or more implementations.

The bus 708 also connects to the input and output device interfaces 714 and 706. The input device interface 714 enables a user to communicate information and select commands to the electronic system 700. Input devices that may be used with the input device interface 714 may include, for example, alphanumeric keyboards and pointing devices (also called "cursor control devices"). The output device interface 706 may enable, for example, the display of images generated by the electronic system 700. Output devices that may be used with the output device interface 706 may include, for example, printers and display devices, such as a liquid crystal display (LCD), a light emitting diode (LED) display, an organic light emitting diode (OLED) display, a flexible display, a flat panel display, a solid state display, a projector, such as a prism projector that may be included in a smart glasses device, or any other device for outputting information. One or more implementations may include devices that function as both input and output devices, such as a touchscreen. In these implementations, feedback provided to the user can be any form of sensory feedback, such as visual feedback, auditory feedback, or tactile feedback; and input from the user can be received in any form, including acoustic, speech, or tactile input.

As shown in FIG. 7, bus 708 also couples electronic system 700 to one or more networks (not shown) through one or more network interface(s) 716. The one or more network interface(s) may include an Ethernet interface, a WiFi interface, a Bluetooth interface, a Zigbee interface, a multimedia over coax alliance (MoCA) interface, a reduced gigabit media independent interface (RGMII), or generally any interface for connecting to a network. In this manner, electronic system 700 can be a part of one or more networks of computers (such as a local area network (LAN), a wide area network (WAN), or an Intranet, or a network of networks, such as the Internet. Any or all components of electronic system 700 can be used in conjunction with the subject disclosure.

Figure 8A:
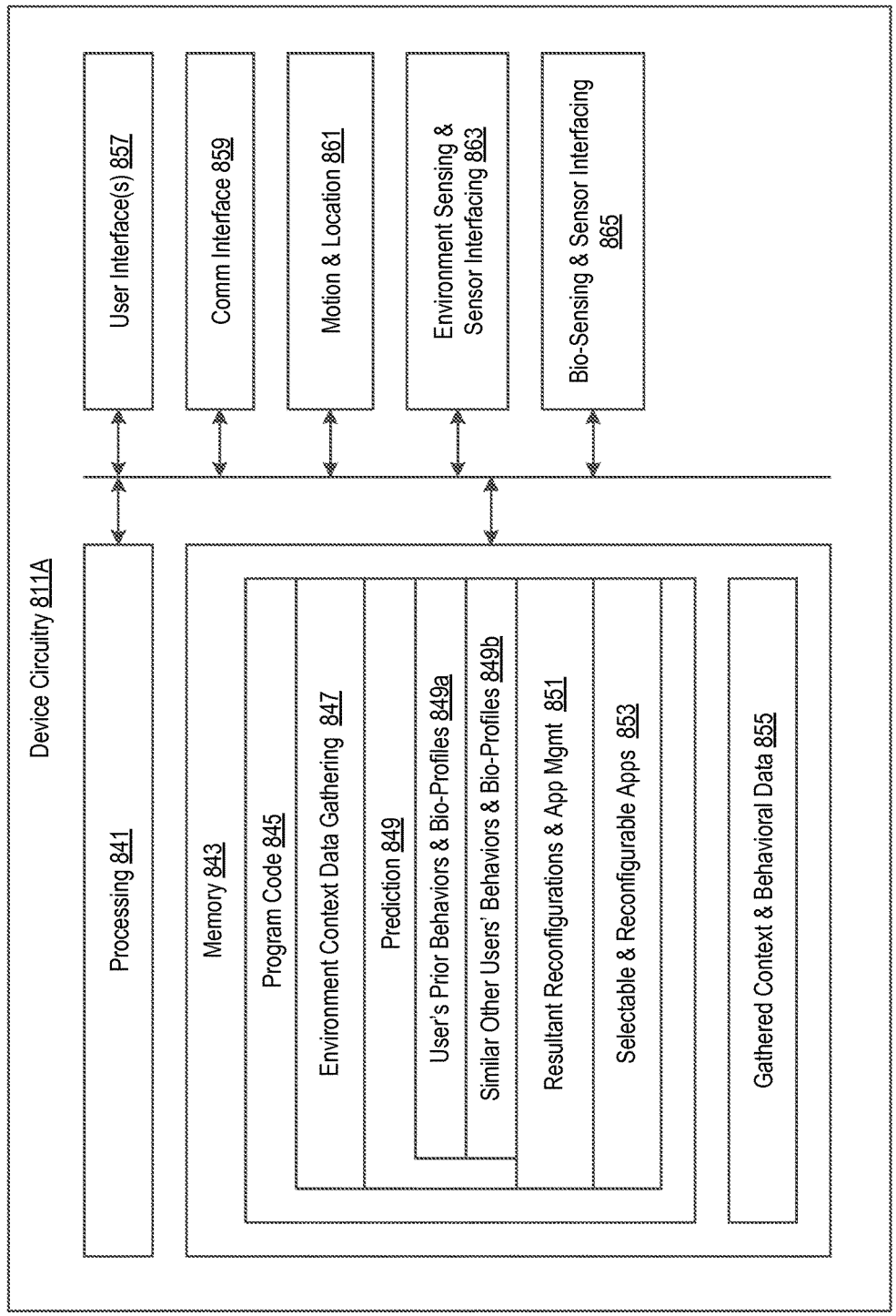
FIG. 8A is a schematic block diagram illustrating one example of circuitry and software within a device (i.e., within a device housing) that supports at least one implementation of the subject technology.

FIG. 8A is a schematic block diagram illustrating one example of circuitry and software within a device (i.e., within a device housing) that supports at least one implementation of the subject technology. Specifically, device circuitry 811A may represent all or part of each of the devices, servers and network devices. It may also be used in whole or in part within any other computing or networking device, system or Thing (e.g., as per the Internet of Things) such as those found in FIG. 9. The device circuitry 811A includes processing circuitry 841, memory 843, user interface circuitry 857, communication interface 859, motion and location sensor interface circuitry 861, environment sensor interface circuitry 863 and bio-sensor interfacing circuitry 865.

The user interface circuitry 857 couples the device circuitry 811A with one or more of the various possible types of user interface elements such as touch-screen assemblies, speakers, microphones, mice, keyboards, keypads, buttons, image/video capture elements and so on. The communication interface 859 couples the device circuitry 811A with one or more external, remote other devices and underlying device circuitry via proprietary or Industry Standard defined wired or wireless communication pathways. The sensor elements and assemblies (although not shown) associated with the sensor interface circuitries 861, 863 and 865 may be integrated within the device circuitry 811A or located at a more beneficial location within, on or outside of the device housing (e.g., via a tether). Such sensor elements and assemblies couple with the device circuitry 811A via the sensor interface circuitries 861, 863 and 865.

The memory 843 stores program code 845 and gathered context and behavioral data 855. The program code 845 includes environment context data gathering code 847, prediction code 849, resultant reconfigurations and application management code 851, and selectable and reconfigurable applications code 853. The prediction code 849 includes user's prior behaviors and bio-profiles 849a and similar other users' behaviors and bio-profiles 849b.

While often being engaged with other processing duties, the device circuitry 811A operates to collect and store in time relationships motion, location, environment, bio, App and user interface data gathered over time. Such collected and stored data being represented in FIG. 8 as the gathered context and behavioral data 855 within the memory 843. Such data may be stored in raw form (as collected), compressed form, or in a processed form that identifies relationships between such data with user behaviors and their associated context. These collection and storage operations are carried out by the processing circuitry 841 in accordance with the environment context data gathering code 847. The processing circuitry 841 collects from various motion, location, environment and bio sensors via the sensor interface circuitries 861, 863 and 865. App usage and data associated with the other processing duties of the processing circuitry 841 is directly collected and stored. In addition, via the communication interface 859, other neighboring and remote devices also deliver for storage additional motion, location, environment and bio sensors data and App and user interface and interaction data.

With all such data storage within the gathered context and behavioral data 855, the processing circuitry 841, pursuant to the prediction code 849, generates the user's prior behaviors and bio-profiles 849a. For example, the gathered context and behavioral data 855 when analyzed might reveal a repetitive, time relationship between a sensed event in one sensor data stream with a sensed event in another sensor data stream. Likewise, a sensed event in one sensor data stream may have a repetitive, time relationship with a particular user interfacing behavior or App operation. A simple version, for example, might involve a repetitive, time relationship involving a first event trigger or duration followed by a delay window and, finally, by a different stream event trigger or duration. The averages and deviations thereof being generated through repetition (e.g., possibly repeating often daily or only several times a year). Once identified, the processing circuitry 841 saves the relationship as one of the user's prior behaviors and bio-profiles 849a, e.g., within a profile database.

In addition to performing both foreground tasks (e.g., often unrelated App and OS duties) and background collection, analysis and profile generation duties, the processing circuitry 841 also utilizes the generated bio-profiles 849a in a predictive manner. By encountering a first event trigger or duration of one of the bio-profiles 849a and knowing the expected time relationship to a second event, the processing circuitry 841 can take a preempting or assisting action to either enhance or simplify the user's experience or to dissuade or distract the user and change the expected outcome. For example, a user with high blood pressure issues may react negatively to certain web browser interaction and positively to adventure movies. Identifying these relationships within profiles, the processing circuitry 841 may react to a blood pressure threshold by attempting to dissuade that particular web browser interaction and possibly direct the user to their TV to watch the adventure film. Thus, it can be appreciated that more complex profiles involve two or more timing relationships, each between two events along with associated preference logic that drives the user from one expected outcome to another or enhances the likelihood of the expected outcome, and, in either case, simplifying the user interactions required.

By testing the user's prior bio-profiles 849a, a likelihood of success can be established. Those deemed unsuccessful even after repeated attempts may be flagged so that they will not be used again. Through user interfacing (e.g., pop up window interaction), the user may be offered the opportunity to prevent the flagging. The user may also review profiles, flag, unflag and further define or modify profiles through a profile user screen interaction as directed by the processing circuitry 841 via the user interface circuitry 857.

Many types of user and environmental actions and activities have bio-impact significance but occur outside the realm of an electronic device, e.g., petting a dog or scolding a child. In other words, they are hidden contexts with predictive relationships with bio-impact significance. That is, such activity can trigger a bio-impact (e.g., elevated heart rate, frown, angry voice or posture, blood sugar balance, etc.), or such activity can be triggered by such bio-impact. To reveal the nature of the hidden context, the processing circuitry 841 in accordance with the program code 845 delivers a pop-up query to request user labeling and event desirability. For example, the processing circuitry 841 may identify a bio-impact and conclude that there is no user-device interaction in time window correlation that could be causing the bio-impact. Instead of discarding such hidden context, the processing circuitry 841 queries the user as to what is happening. The user might respond "petting my dog." The query continues asking the user about the repeatability of such activity, likely duration, location limitations, and desirability relating to repeating behaviors. Thereafter, the processing circuitry 841 can weave such user gathered details into a fully functional profile that can be used to dissuade the user from other activities, alter a user's bio events and status, and can help enhance or simplify such activities (e.g., offer advertising to purchase pet grooming items or chew toys, or offer ads for identifying a breed or purchasing a dog).

Similarly, the processing circuitry 841 can query a user to identify preference logic. The bio-impacting relationships are identified automatically by the processing circuitry 841, and, without more, can be utilized by the processing circuitry 841 to enhance or assist an upcoming user behavior. For example, a user that always relaxes, lowering blood pressure, by turning on the TV and seeks a family movie channel after returning home for work can be automatically identified. The processing circuitry 841 need not understand the nature of the relationship, but merely reacts to a high blood pressure status and arrival to a home location by sending command signals via the communication interface 859 to turn on the television and select a family movie channel so that the user is drawn to relax and view. However, without considering that low blood pressure status is beneficial when above a certain threshold, the processing circuitry 841 cannot make more appropriate decisions. For example, it could be equally likely that turning the television to a honor movie channel might drive blood pressure higher. To know whether to pursue the honor or family channel "coaxing," the processing circuitry 841 draws preference logic or preference data from (i) hard-coding by programmers (that understand underlying goals), (ii) programmer defined data, (iii) from user interaction, and (iv) from data associated with the sensing elements or sensing devices. Such preference logic or preference data can also be generated within another user's device circuitry and communicated via the communication interface 859 for storage as the similar other users' behaviors and bio-profiles 849b.

A series of data streams originate from any device associated with or in vicinity of the user. Each data stream represents one of time stamped motion, location, environmental and bio sensor data and App, OS (Operating System) or user input and interaction data. These are stored within the memory 843 for use by the processing circuitry 841 in its identification of event states (triggers or expectations) within each stream. With event states identified, the processing circuitry 841 attempts to identify repetitive relationships between two or more streams. Some event states that lead off an event sequence over time are referred to as a triggering event. Expected middling and following event states are referred to as triggered events. Also in addition to levels and level ranges, an event state may also be defined as a downward or upward trend and other more complex stream data behaviors.

In addition to self-identified triggering and triggered events extracted from analyzing and time correlating stream data, the processing circuitry 841 also receives event state definitions from the stream sources themselves. For example, a heart rate sensing wearable sends not only heart rate stream data, but can identify preference logic and data along with corresponding one or many event states such as those acceptable for the user while inactive (sleeping, sitting) and active (walking, running). A sensor data stream can also identify such event states within the sensor data stream, or define its sensor data stream as comprising only such event states without more (e.g., where such associated processing duties occurs within such sensor device). Alternatively, such event state definitions and preference logic and data can be downloaded or otherwise loaded as a software based driver (or embedded within an App or OS via hard coding or via data) into the memory 843 for pairing with any one or more of the data streams stored within the memory 843 as the gathered context and behavioral data 855.

To determine from one sensor's data stream an event state, the processing circuitry 811A automatically attempts to identify deviations, volatility and abnormalities from average sensor sample value data over time. Such identification can itself be used for cross-sensor data to compare with other (e.g., being defined by meeting or exceeding threshold value or threshold change or rate of changes once, repeatedly, or continuously over a period of time with or without some type of averaging). The processing circuitry 811A stores these "self-identified" event states (triggering events and triggered events), within the memory 843 as part of the bio-profiles 849a. Sensor, user interface, App, OS, etc., related deliveries of event states are also stored as part of the bio-profiles 849a. Other event states of relevance (those being triggering and triggered events) associated with other users' are also stored with the memory 843 as part of the bio-profiles 849b.

The preference logic and data is not needed for event data with an associated bio-impact or user behavior that is not undesirable. Thus, without such knowledge of desirability, the processing circuitry 841 merely identifies a trigger event and helps to coax, enhance, setup or simplify a user's subsequent behavior or interaction associated with the expected corresponding triggered event—even in advance of expecting such triggered event to occur. If preference logic and data is available, the processing circuitry 841 appropriately alters its response to the triggering event by either (i) more aggressively attempting to coax, enhance, setup or simplify a user's subsequent behavior or interaction, (ii) attempts to dissuade through direct user pop-up interaction, or (iii) offers coaxing alternatives that include setup and simplification of the user's alternate, subsequent behavior or interaction. With the latter, the processing circuitry 841 selects such alternatives from those identified by stream data—often from user interaction data associated with Apps and various devices. Where a single triggering event is expected to lead to two or more triggered events wherein the most likely is undesired, the processing circuitry 841 chooses the most desirable and most likely acceptable (based on offer/acceptance frequency) from the other triggered events. Alternates can also be selected when contextually appropriate even though they have no relationship to a pending (recently occurring) triggering event. Such unrelated alternatives may thwart the effect of the triggered event in replacing with another desired, positive behavior.

Figure 8B:
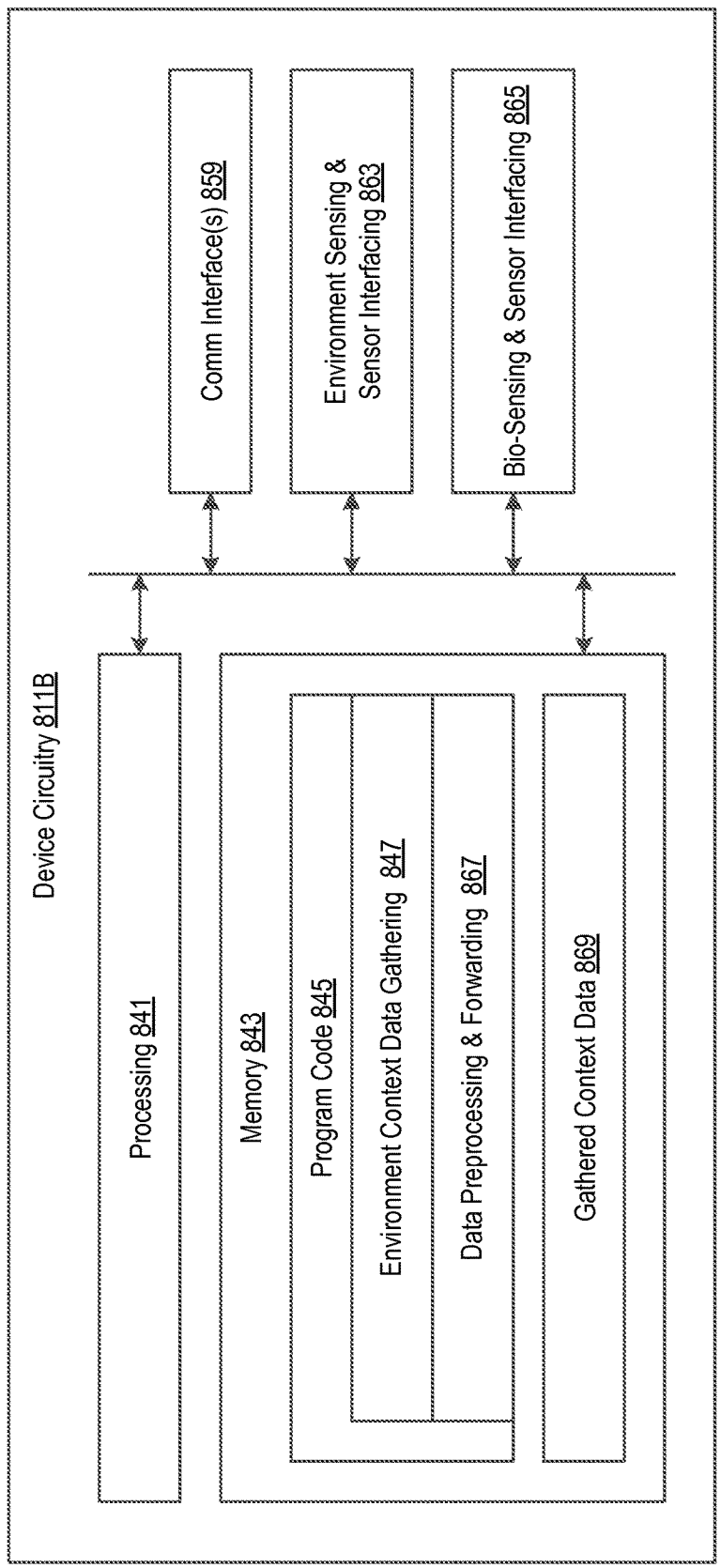
FIG. 8B is a schematic block diagram illustrating another example of circuitry and software within a device (i.e., within a device housing) that supports at least one implementation of the subject technology.

FIG. 8B is a schematic block diagram illustrating another example of circuitry and software within a device (i.e., within a device housing) that supports at least one implementation of the subject technology. Specifically, device circuitry 811B may represent all or part of any device that includes sensor data collection, such as a Thing, wearable, networking devices, smartphone, tablet, etc., as illustrated, for example, in FIGS. 1 and 9. Regarding functionality and associated circuitry and software, the device circuitry 811B comprises one example of a subset of that found within the device circuitry 811A of FIG. 8A. Within that subset, the functionality described in correspondence with FIG. 8A is fully applicable to that of FIG. 8B. Other subsets are also possible as FIG. 8B is merely but one possibility.

The device circuitry 811B captures, time-stamps, and selectively performs pre-processing of raw sensor stream data before forwarding same via a communication interface 859 to the device circuitry 811A (FIG. 8A) for use in bio-impact profiling and prediction. More specifically, much like the device circuitry 811A (FIG. 8A), the device circuitry 811B includes processing circuitry 841, memory 843, the communication interface 859, environment sensor interface circuitry 863 and bio-sensor interface circuitry 865. Here, the processing circuitry 841 has no need to carry out the bio-impact profiling and prediction as it will be done by another device. Instead, the processing circuitry 841 focuses on any foreground tasks needed to be handled while coordinating (often in background) the collection and time stamping of raw sensor data from the sensor interface circuitries 863 and 865. To carry out time-stamping, the processing circuitry 841 also attempts to synchronize its clocking with any or all of other data stream collection devices and devices that performs bio-impact profiling or prediction—at least those involved in underlying device group behavioral and bio-impact related activities for the subject user. In this way, the device circuitry 811A (FIG. 8A) can receive time stamped data streams from several devices each configured with the device circuitry 811B and be able to conduct cross data stream event correlations with legitimate timing relationships.

The processing circuitry 841 stores within the memory 843 the raw sensor data from the sensor interface circuitries 863 and 865 with time stamping (or otherwise associated or stored in or with timing relationships or indications) as the gathered context data 869. The memory 843 also stores the program code 845 which further includes data preprocessing & forwarding code 867. In some configurations, the gathered context data 869 (i.e., the raw, time-stamped sensor data streams) can be directly delivered to a remote device via the communication interface 859 even without time stamping if real time (which may not require the gathered context data 869 to be more than a small, outgoing communication queue. In other cases, the processing circuitry 841 performs data pre-processing to compress and forward a sensor stream with or without event identification, depending on a selected mode of operation. Likewise, depending on the mode, the processing circuitry 841 delivers preference logic and/or data associated with a given sensor stream to another device via the communication interface 859 to assist with such other device's bio-impact and prediction processing. Selecting the mode of operation of the processing circuitry 841 can be made on the fly (adaptively) through responding to commands received from such other device via the communication interface 859.

As can be appreciated, even the device circuitry 811A can be configured to perform similarly through similar mode selections. Thus, when a first plurality of devices each with the device circuitry 811A encounter a second plurality of devices each with the device circuitry 811B, through mode selection each of the duties of data stream generation, pre-processing of data streams (if any), bio-impacting profile generation, real time triggering event detection, real time response through selective profile application, and so on can be allocated to appropriate and capable ones of the devices within the overall group. Some may discontinue sensor stream generation and enter sleep modes to save power with another parallel sensor in another device taking over the data stream generation requirements. Some may handle no sensor processing but merely handle profile generation. Others may only detect or respond to a triggering event detection by coordinating multiple device actions through group commands. In other words, various networking nodes (e.g., switches, access points, Things, cloud and server systems, hand held and wearable devices, computers, home appliances, entertainment equipment, and so on), can be configured with some or all portions of the hardware and software illustrated in FIGS. 8A and 8B and further configured by mode selection to enable, disable or otherwise configure such hardware and software to meet a current, dynamic need associated with at least one but often many devices. All such devices forming a functional group to carry out the overall bio-impact related process. Such groupings of course changing as underlying devices are added or dropped based on mobility, power resource status, alternate duty load balancing, communication link status, and so on.

Figure 9:
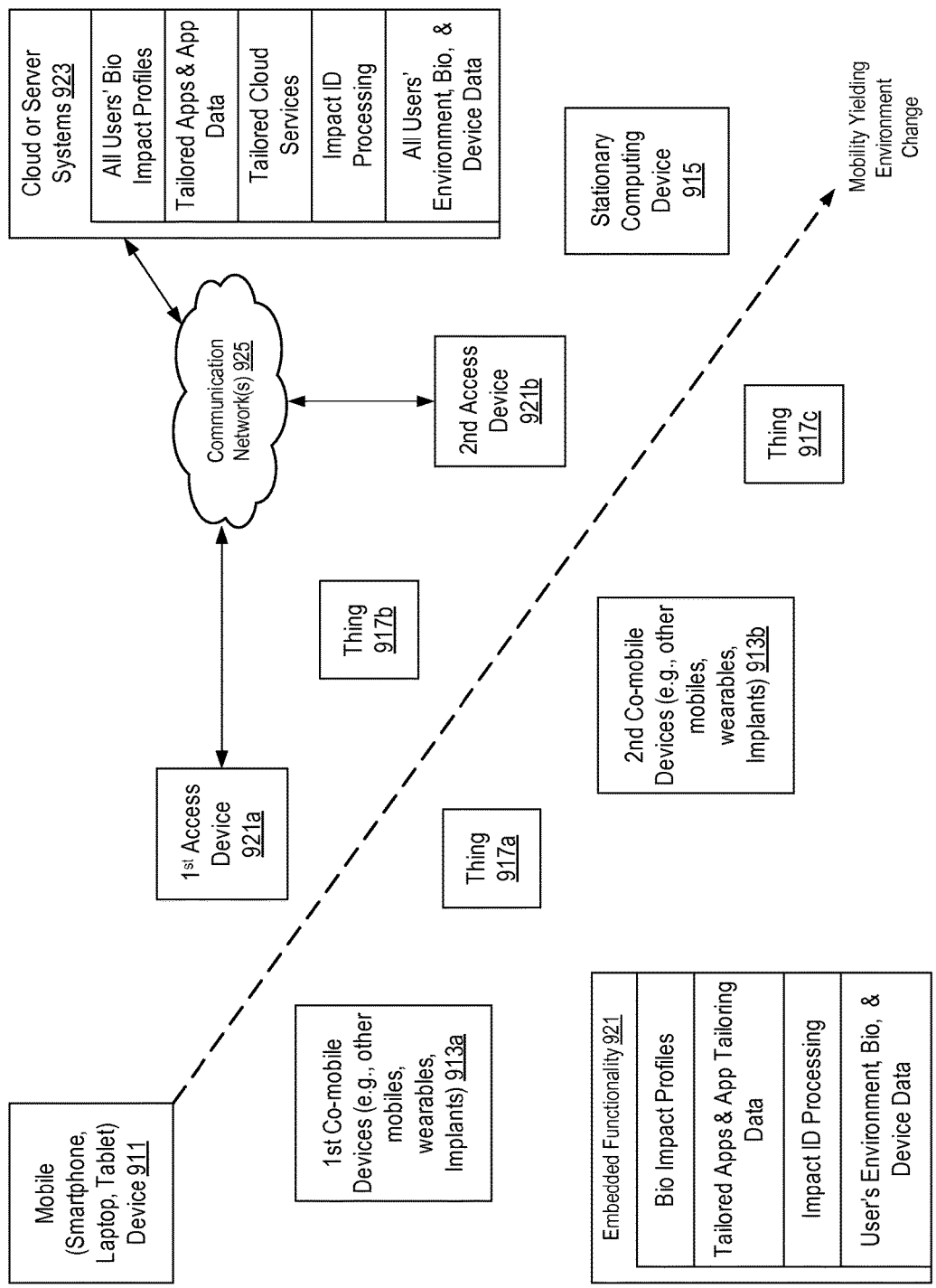
FIG. 9 is a block diagram illustrating an example of bio-impact processing and dynamic underlying duties assignment that supports at least one implementation of the subject technology.

FIG. 9 is a block diagram illustrating an example of bio-impact processing and dynamic underlying duties assignment that supports at least one implementation of the subject technology. Therein, a mobile device 911, such as a tablet, smartphone or laptop, is carried by a roaming user from location to location over time as indicated by the dashed arrowed line. Initially, as illustrated, the mobile device 911 has no network or direct communication pathways to any other device so all bio-impact related processing is performed internally. For example: (i) all built in environmental and bio-sensors are captured, (ii) user input data is captured, (ii) App usage and state information is captured; (iii) all captured data is processed to identify triggering events and triggered events, (iv) preference logic and data are applied when available to attempt to dissuade a user from carrying out an otherwise expected triggered events; (v) for some triggering events, the mobile device 911 attempts to coax the user toward the expected (triggered event) behavior through setup, enhancement and otherwise simplify the user's interactions needed to begin and carry out the expected behavior; and (vi) prompt the user for hidden context related information and data to define preference logic and preference data.

As location and movement sensors and connectivity capabilities change, the duty assignment and scope changes. For example, when moving in range of the first access device 921a, the mobile device 911 gains access to not only those resources of the first access device 921a itself, but also to intermediate switching and routing node resources (not shown), resources of cloud or server systems 923, and resources of any other networked device illustrated. To enlist the services of other devices, the mobile device 911 sends requests for capability and cost data to any device under consideration. In this example, the mobile device 911 makes the request to the first access device 921a and cloud or server system 923 with the goal being to minimize battery and processing resource consumption. Through coordinated interactions amongst the three: (i) the cloud or server system 923 is assigned the task of identifying new profiles based on stream data communicated from the mobile device 911, the duty of the first access device 921a is to identify triggering events from the set of profiles, forward received data streams to the server system 923, and communicate identified triggering events to the mobile device 911; and (iii) the mobile device 911 forwards all data streams and responds to triggering event identification (by the first access device 921a) by attempting to coax, dissuade or enhance an expected behavior as defined by the underlying profile.

Again, as location and movement further bring about, the mobile device 911, while still connected to the first access device 921a, encounters the first co-mobile device 913a. For example, the user decides to don a wearable device while still carrying the mobile device 911. Because the first co-mobile device 913a may have greater battery resources or may produce better sensor data streams, it is selected to carry out data stream responsibilities for at least some of the sensors within the mobile device 911. Once collected, the data streams can be forwarded directly to the first access device 921a or relayed thereto through the mobile device 911 (or through any other available device, e.g., where a mesh interconnection is available). The corresponding "like-type" sensors within the mobile device 911 can then be shut down or still forwarded to increase overall accuracy.

As battery resources wane or processing resource load balancing require, the mobile device 911 may also adapt by nominating the first co-mobile device 913a to carry out much of its other duties—those associated with responding to triggering event identification by attempting the coaxing, dissuading or enhancement of the expected behaviors. Such duties may all require an interaction with the mobile device 911 (via communicated commands) but may also involve carrying out internal commands as such coaxing, dissuading and enhancement can be performed in part by the first co-mobile device 913a itself.

Later, through further roaming, Things 917a and 917b are encountered. The Thing 917a being an environmental sensor, such as a temperature sensor, while the Thing 917b a refrigerator, for example. Once encountered, both Things 917a and 917b may begin to send data streams directly or through relaying to the first access device 921a for processing. Once received, further bio-profile relationships become available for consideration, and the cloud or server system 923 gains access to further data stream through which even further bio-relationships (bio-profiles) can be identified and commissioned back to the first access device 921a for use in identifying triggering events from real time data streams.

Further roaming may find a user encountering a second co-mobile device 913b being donned along with stream drop outs along with direct connectivity to Things 917a and 917b and the first access device 921a. Picking up network access through a second access device 921b offers multiple options to going forward adaptation. First, the mobile device 911 upon losing (or upon anticipating the loss) connectivity with the first access device 921a, may still retain status quo functionality by communicating with the first access device 921a indirectly—through the second access device 921b to the first access device 921a via one or more communication networks 925. Handover of such functionality can also be selected where the mobile device 911 and the second access device 921b coordinate handover either via the underlying wireless cells or via the communication networks 925. Such handover may only be in part, for example, where the second access device 921b handles some data stream processing or forwarding, while the first access device 921a retains the rest of the duties.

Likewise, as some data streams drop out, others such as that from a Thing 917c, might become available. When some drop, certain related bio-profiles may become unavailable as they may be based on the dropped streams. When added, a data stream becomes available for pre-identified bio-profile checking (if any exist) and for identifying further bio-profiles (e.g., in this example, by the cloud or server systems 923).

Further mobility yields an encounter with a stationary computing device 915 such as an in-home NAS (Network Attached Storage) system, a home or enterprise server, or a desktop computer. This encounter causes yet a further adaptation which may result in the cloud or server system 923 handing off its duties or portions thereof to the stationary computing device 915. Handovers with adaptation on overall bio-impact processing services offered may take place nearly immediately upon new device encounters or over time.

To support such dynamic operation, the devices 911, 913a-b, 917a-c, 921a-b and 915 are each configured with embedded functionality 921 through hardware and software such as that set forth in FIGS. 8A and 8B. In particular, such embedded functionality 921 includes one or more of storage of defined bio-impact profiles, bio-profile tailored Apps & bio-profile tailoring App, defined bio-impact profile based triggering event identification capabilities, full bio-impact profile generation capabilities, and storage of user's environment, bio and device (App, OS and user input and interaction) data.

Likewise, the cloud or server systems 923 have various embedded functionality supporting bio impact processing. For example, a cloud service may be provided that can be tailored based on bio-impact profiles specific to one user, all users or a group of similar users. Commands to tailor may originate from any of the devices illustrated in FIG. 9 (or underlying the communication networks 925) or internally from within the cloud or server systems 923 (e.g., where the server systems 923 itself carries out the duty of identifying triggering events within real time data based on pre-defined profiles. Similarly, Apps can be tailored (through hard coding or via App data) that can then be delivered to one of the devices of FIG. 9 for execution. That is, a bio-impact profile may define a coaxing, dissuading or enhancing experience via a specifically tailored App or App behavior that is created on the fly or beforehand for download and execution when so commanded. OS (Operating System) tailoring data can also be similarly communicated, for example, when coaxing is to be conducted by the OS. Any other tailored program element or element tailoring data can also or alternatively be used.

The cloud or server systems 923 also provides for distribution of bio-impact solutions by sharing predefined bio-impact profiles. Such predefined profiles include those developed by other users in the manner set forth herein, but also include hard-coded profiles defined by programmers via program code or program data. Thus, predefined profiles originate from (i) the user's equipment and environment, (ii) other and similar other users' equipment and environments, or (iii) through programmers' direct coding or data definitions.

Figure 10:
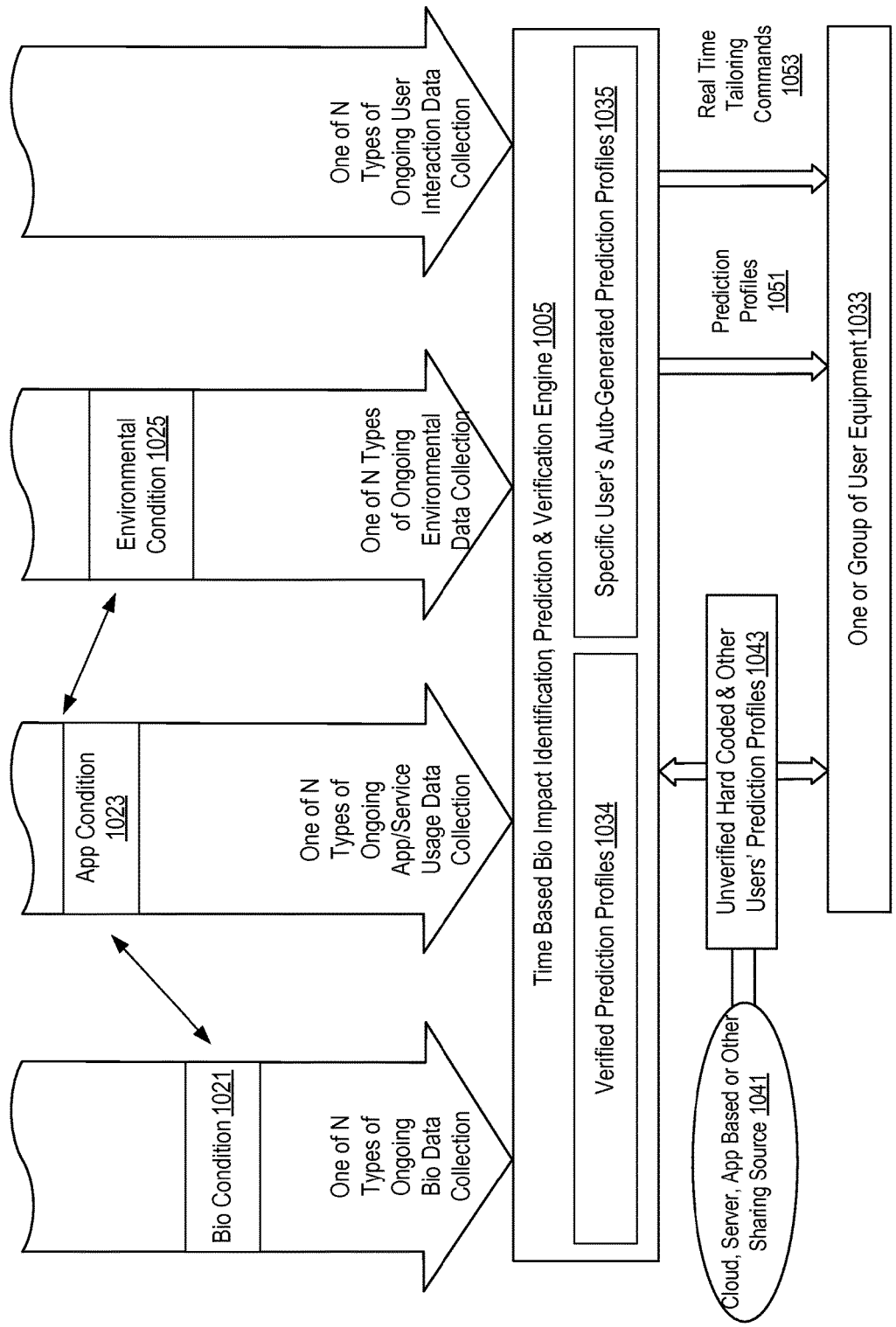
FIG. 10 is a block diagram illustrating one example of triggering event identification based on all types of bio-impact profiles that supports one or more implementations of the subject technology.

FIG. 10 is a block diagram illustrating one example of triggering event identification based on all types of bio-impact profiles that supports one or more implementations of the subject technology. Therein, a time based bio impact identification, prediction and verification engine 1005 receives several data streams from which new bio-profiles are generated and previously defined profiles are applied. The functionality of the engine 1005 can be distributed across many devices or run fully within one as preconfigured, initially set up, or through handover operations, as described previously. The engine 1005 represents another way of viewing the bio-related functionality carried out by the device circuitries 811A (FIG. 8A) and 811B (FIG. B).

Specifically, as illustrated, the engine 1005 receives four categories of data streams and, within each category, one or multiple data streams can be found. The four categories being 1) bio sensor related data streams, 2) software and device usage related data streams, 3) environmental sensor related data streams, and 4) user input and interaction data streams. No time stamping of data stream content is needed if virtually real time delivery of all data streams upon collection occurs. If this isn't the case, time stamping within data stream content is applied. Upon receipt by the engine 1005, time stamping may still be performed for all un-stamped data stream data to accommodate longer term evaluations (e.g., for new bio-profile identification). Thereafter, three processes take place. The first is to attempt to identify new bio-profiles from all of the incoming data streams that can be used for the first process. The second is to attempt to match all predefined bio-profiles with one or more relevant incoming data streams. Lastly, the engine 1005 attempts to verify other user's bio-profiles to make decisions about long term inclusion in the overall active profile set.

Regarding the first process, the engine 1005 attempts to identify data "conditions" by identifying deviations, volatility and statistical abnormalities, e.g., from averaging with various windows of raw values, rates of change, and so on. These conditions may or may not comprise a triggering or a triggered event from a bio-profile point of view. In addition to those generated by the engine 1005, conditions can be defined and delivered from other sources, such as by the source of the data stream itself. For example, a blood pressure sensor may have a manufacturer's defined set of condition parameters that can be communicated in various ways to the engine 1005, including as part of setup or even within the data stream itself (as setup or midstream as conditions occur as identified by the data stream source).

With all conditions identified in each of the data streams based on analysis or through received condition parameters, a time based analysis to find inter and intra stream repeatable relationships between conditions can be exposed along with probabilities of triggering type conditions ("triggering events") actually yielding expected triggered type conditions ("triggered events"). This may be as simple as one triggering event causing a triggered event thirty seconds later at a 62% likelihood. More complexity enters the scene as it may take two or more conditions to trigger one or more other conditions. All such complexity falls within the definition of each predefined bio-profile. Once identified and reduced to a bio-profile format, the engine 1005 may initiate a user interaction to query for preference logic and data, as described previously. Any retrieved preference logic and data is combined into the bio-profile format. Both bio-profiles with and without preference logic and data are saved as predefined bio-profiles, the specific user's generated prediction profiles 1035, for use by the second process performed by the engine 1005.

For example, the engine 1005 identifies an App condition 1023 as a triggering event that when associated with a high room temperature, the environmental condition 1025 triggers within 2 minutes a high heart rate condition 1021. For example, playing a video game during extremely hot weather may cause a child with a heart defect to enter fibrillation. To avoid the bio condition 1021 which is the expected triggered event, an alternative might be offered (as defined in supplemental response information). The engine 1005 first recognized the relationship and constructs a predefined profile in response. Similarly, a bio condition may comprise a triggering event of another bio condition or of an App condition. For example, when someone's blood pressure is dropping, they may tap a thermostat to check and raise the ambient temperature. A profile might identify the drop in blood pressure, automatically adjust the thermostat upward, and further prompt the user through pop-ups that they may need to take their medication. Also, as mentioned previously, some events may correspond to hidden contexts which can be probed through user querying to build more appropriate bio-profiles. Thus, all bio-profiles can involve one or more biometric data triggering and biometric data triggered events. Non-bio related profiles can also be integrated and supported by the engine 1005 and function in similar ways as the bio-profiles as described herein.

Regarding such second process, the engine 1005 evaluates in real time only those streams that are needed (and only when needed) to attempt to identify conditions that seem to fall within the triggered event definitions of the active, the predefined profiles 1035. Once identified, the engine 1005 will take actions based on whether or not preference logic and data are present and in conformance therewith if present. For example, if not present, the engine 1005 responds to an identification of a condition corresponding to a triggering event of a first bio-profile by carrying out actions that will help coax, enhance, setup and otherwise prepare for the expected triggered condition defined within the bio-profile. Similarly, if preference logic and data are present, the engine 1005 may respond in conformance to attempt to dissuade or distract the user or otherwise attempt to prevent the expected triggered event from occurring.

In addition, some predefined profiles also include supplemental response information as to what steps are to be taken to avoid, coax or enhance an expected triggered event. Like the preference logic and data, this supplemental information can be gathered through (i) query interaction with the user, (ii) downloaded or selected from a set of predefined alternative options, and (iii) selected based on secondary, less likely expected results (as mentioned previously). Selections based on such gathered supplemental information options can be made automatically by the engine 1005 or comprise part of a user interaction wherein the user makes the choice. For example, the engine 1005 might identify a triggering event and deliver a pop window to the user to offer up several device environment configurations to support a corresponding several user activities that may or may not include the otherwise expected triggered event (depending on the preference logic and data).

Regarding the third process, the engine 1005 receives unverified hard coded and other users' bio-profiles 1043 from a cloud, server, App based or other sharing source 1041. These bio-profiles include triggering event and triggered event definition data, and, depending on the particular profile, may include preference logic and data and supplemental information regarding the response to an identified triggering event. Because such profiles are unverified or untested with the current user, they may prove ineffective as the triggered event and even the underlying triggering event may not occur. Even so, because of the complexity of creating enriched bio-profiles, it is worthwhile to share those that are effective with all or at least similar users to try out. This try-out, or verification attempt, is carried out by the engine 1005. If attempts to identify a shared profile's triggering event prove fruitless, such shared profile can be discarded or flagged as inactive. If such triggering event is detected, a search for significant statistical repeatability in producing the corresponding triggered event is sought. If not found, again, the shared profile can be discarded or flagged as inactive. Lastly, if both the triggered and triggering events are identified, then the prediction profile can be flagged as verified and represented by verified prediction profiles 1034.

The engine 1005 also delivers prediction profiles 1051 to some of the one or groups of user equipment 1033 for their internal use in bio-profile processing. To some other of the ones and groups of user equipment 1033, the engine 1005 delivers real time tailoring commands 1053 that attempt to adapt a user's current environment to enhance, adapt or avoid an expected user's behavior.

Implementations within the scope of the present disclosure can be partially or entirely realized using a tangible computer-readable storage medium (or multiple tangible computer-readable storage media of one or more types) encoding one or more instructions. The tangible computer-readable storage medium also can be non-transitory in nature.

The computer-readable storage medium can be any storage medium that can be read, written, or otherwise accessed by a general purpose or special purpose computing device, including any processing electronics and/or processing circuitry capable of executing instructions. For example, without limitation, the computer-readable medium can include any volatile semiconductor memory, such as RAM, DRAM, SRAM, T-RAM, Z-RAM, and TTRAM. The computer-readable medium also can include any non-volatile semiconductor memory, such as ROM, PROM, EPROM, EEPROM, NVRAM, flash, nvSRAM, FeRAM, FeTRAM, MRAM, PRAM, CBRAM, SONOS, RRAM, NRAM, racetrack memory, FJG, and Millipede memory.

Further, the computer-readable storage medium can include any non-semiconductor memory, such as optical disk storage, magnetic disk storage, magnetic tape, other magnetic storage devices, or any other medium capable of storing one or more instructions. In one or more implementations, the tangible computer-readable storage medium can be directly coupled to a computing device, while in other implementations, the tangible computer-readable storage medium can be indirectly coupled to a computing device, e.g., via one or more wired connections, one or more wireless connections, or any combination thereof.

Instructions can be directly executable or can be used to develop executable instructions. For example, instructions can be realized as executable or non-executable machine code or as instructions in a high-level language that can be compiled to produce executable or non-executable machine code. Further, instructions also can be realized as or can include data. Computer-executable instructions also can be organized in any format, including routines, subroutines, programs, data structures, objects, modules, applications, applets, functions, etc. As recognized by those of skill in the art, details including, but not limited to, the number, structure, sequence, and organization of instructions can vary significantly without varying the underlying logic, function, processing, and output.

While the above discussion primarily refers to microprocessor or multi-core processors that execute software, one or more implementations are performed by one or more integrated circuits, such as ASICs or FPGAs. In one or more implementations, such integrated circuits execute instructions that are stored on the circuit itself.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that any specific order or hierarchy of blocks in the processes disclosed is an illustration of example approaches. Based upon design preferences, it is understood that the specific order or hierarchy of blocks in the processes may be rearranged, or that all illustrated blocks be performed. Any of the blocks may be performed simultaneously. In one or more implementations, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

As used in this specification and any claims of this application, the terms "base station", "receiver", "computer", "server", "processor", and "memory" all refer to electronic or other technological devices. These terms exclude people or groups of people. For the purposes of the specification, the terms "display" or "displaying" means displaying on an electronic device.

As used herein, the phrase "at least one of" preceding a series of items, with the term "and" or "or" to separate any of the items, modifies the list as a whole, rather than each member of the list (e.g., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The predicate words "configured to", "operable to", and "programmed to" do not imply any particular tangible or intangible modification of a subject, but, rather, are intended to be used interchangeably. In one or more implementations, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

The word "exemplary" is used herein to mean "serving as an example, instance, or illustration." Any embodiment described herein as "exemplary" or as an "example" is not necessarily to be construed as preferred or advantageous over other embodiments. Furthermore, to the extent that the term "include," "have," or the like is used in the description or the claims, such term is intended to be inclusive in a manner similar to the term "comprise" as "comprise" is interpreted when employed as a transitional word in a claim.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

What is claimed is:

1. A method performed by a processing device, the method comprising:
   generating a user behavioral predictive model based at least on historical behaviors of a user and associated historical environmental profiles, at least one of the historical behaviors being determinable from sensor data received from a sensor device associated with the user;

obtaining an environmental profile of an environment associated with a user;

determining a predicted behavior of the user by applying the environmental profile to the user behavioral predictive model;

determining information related to the predicted behavior of the user;

filtering the information related to the predicted behavior of the user based at least in part on a recent behavior of the user; and providing the information related to the predicted behavior to the user.

2. The method of claim 1, further comprising:

obtaining a current biometric profile of the user based at least on biometric data received from the sensor device, wherein the sensor device is coupled to the user;

determining a suggested behavior of the user based at least on the environmental profile and the current biometric profile of the user; and performing an action to facilitate conforming the predicted behavior of the user to the suggested behavior of the user.

3. The method of claim 1, further comprising:

receiving a behavioral policy associated with the user;

determining whether the predicted behavior of the user conforms with the behavioral policy; and impeding the predicted behavior when the predicted behavior does not conform to the behavioral policy.

4. The method of claim 1, further comprising:

facilitating the predicted behavior of the user.

5. The method of claim 4, further comprising:

receiving biometric data from the sensor device associated with the user; and further filtering the information related to the predicted behavior of the user based on the biometric data.

6. The method of claim 1, wherein the environmental profile comprises at least one of a location, a time of day, proximal device information, or recent behavioral information.

7. The method of claim 6, wherein obtaining the environmental profile associated with the user comprises:

receiving data from at least one of the sensor device associated with the user or a proximal device that the user is interacting with; and obtaining the environmental profile associated with the user based at least on the received data.

8. The method of claim 1, further comprising:

determining an expected biometric profile of the user based at least on the environmental profile;

obtaining a current biometric profile of the user; and performing an action to facilitate conforming the current biometric profile of the user to the expected biometric profile.

9. The method of claim 8, further comprising:

obtaining another current biometric profile of another user; and performing the action that is expected to facilitate conforming the current biometric profile of the user and the another current biometric profile of the another user to the expected biometric profile.

10. The method of claim 8, further comprising:

obtaining the current biometric profile of the user by receiving biometric data from the sensor device, wherein the sensor device is coupled to the user; and receiving sensor data from at least one sensor device to obtain the environmental profile of the environment.

11. The method of claim 8, further comprising:

generating a user biometric model based at least on a plurality of recommended biometric profiles associated with a plurality of environment profiles, the plurality of recommended biometric profiles being adjusted based at least on historical biometric profile data of the user; and determining the expected biometric profile of the user by applying the environmental profile to the user biometric model.

12. The method of claim 8, further comprising:

receiving a plurality of biometric profiles of the user that are mapped to a plurality of behaviors of the user; and determining a biometric profile adjustment for conforming the current biometric profile to the expected biometric profile, wherein performing the action facilitates one of the plurality of behaviors of the user that is mapped to one of the plurality of biometric profiles that achieves the biometric profile adjustment.

13. The method of claim 8, wherein the environment is associated with additional users and the method further comprises:

receiving expected biometric profiles and current biometric profiles of the additional users from devices of the additional users; and performing the action to facilitate conforming the current biometric profiles of the additional users and the user to the expected biometric profiles of the additional users and the user, respectively.

14. The method of claim 13, further comprising:

assimilating preferences of the additional users received from the devices of the additional users; and performing the action to facilitate the conforming based at least in part on the assimilated preferences of the additional users.

15. The method of claim 14, further comprising:

determining a subset of the preferences that are shared by a threshold number of the additional users; and performing the action to facilitate the conforming based at least in part on the subset of the preferences of the additional users.

16. The method of claim 14, further comprising:

providing, for display, the preferences of the additional users;

receiving user input with respect to the displayed preferences of the additional users; and performing the action to facilitate the conforming based at least in part on the received user input.

17. The method of claim 8, further comprising:

gathering and storing time-related data, the time-related data including bio-sensing data, user interaction data and software application data;

processing the time-related data to identify bio-impacting relationships from which the expected biometric profile of the user is determinable;

identifying the current biometric profile from the bio-sensing data; and responding to the identification by performing the action in an attempt to alter future bio-sensing data.

18. The method of claim 8, further comprising:

storing, with a timing relationship, first data, the first data including bio-sensing related data and software application related data gathered over a period of time;

processing the first data to identify software application related data as having a first bio-impact; and performing the action to cause a future generation of the software application related data to cause the first bio-impact in order to facilitate conforming the current biometric profile of the user to the expected biometric profile.

19. The method of claim 8, further comprising:
storing, with a timing relationship, gathered data, the gathered data including bio-sensing related data and device operational data collected over time;
processing the gathered data to identify a predictive association between a first portion of the bio-sensing related data and a first portion of the device operational data; and
performing the action to cause a future generation of the device operational data in response to obtaining the current biometric profile of the user, wherein the current biometric profile of the user comprises future counterparts of the first portion of the bio-sensing related data.

20. The method of claim 19, wherein conforming the current biometric profile of the user to the expected biometric profile of the user comprises maintaining the current biometric profile of the user.

21. The method of claim 19, wherein the action comprises at least one of sending a communication to a remote device, providing an offer to a user, performing a software reconfiguration, or performing a software selection.

22. The method of claim 19, further comprising:
process the gathered data to identify the predictive association between the first portion of the bio-sensing related data, the first portion of the device operational data, and at least one non-bio-sensing context information item.

23. The method of claim 19, wherein the gathered data originates from at least one of within the processing device or from other environmental devices.

24. A computer program product comprising instructions stored in a tangible computer-readable storage medium, the instructions comprising:
instructions for obtaining a user behavioral predictive model that is configured to predict user behavior based at least on a biometric data item collected from a user;
instructions for collecting at least one current biometric data item from the user;
instructions for applying the at least one current biometric data item to the user behavioral predictive model to determine a predicted user behavior; and
instructions for providing information to the user based at least on the predicted user behavior and an environmental variable associated with the user.

25. The computer program product of claim 24, wherein the environmental variable is indicative of at least one of a location of the user, a time of day, a device in proximity to the user, data received from the device in proximity to the user, or a recent behavior performed by the user.

26. The computer program product of claim 24, wherein the instructions for providing the information related at least to the predicted user behavior and the environmental variable associated with the user further comprises:
instructions for determining a set of information that may be relevant to the user based at least on the predicted user behavior; and
instructions for selecting the information from the set of information based at least on the environmental variable.

27. The computer program product of claim 24, wherein the instructions for obtaining the user behavioral predictive model further comprises:

instructions for receiving a plurality of historical user behavioral data items that describe a plurality of user behaviors performed by the user, wherein each of the plurality of historical user behavioral data items is associated with at least one of a plurality of biometric data items that was collected temporally proximal to a time when each of the corresponding plurality of user behaviors was performed by the user; and
instructions for generating the user behavioral predictive model based at least in part on the plurality of historical user behavioral data items and the associated plurality of biometric data items.

28. The computer program product of claim 27, the instructions further comprising:
instructions for augmenting the user behavioral predictive model based at least on a location of the user at the time when each of the plurality of user behaviors were performed by the user, wherein the augmented user behavioral predictive model is configured to predict user behavior based at least on the at least one biometric collected from the user and a current location of the user when the biometric data item is collected.

29. The computer program product of claim 28, wherein at least one of the plurality of historical user behavioral items is associated with a set of biometric data items collected over a period of time that collectively describe a biological rhythm.

30. A method performed by a processing device, the method comprising:
storing, with a timing relationship, data, the data including bio-sensing data and software application data gathered over a period of time;
processing the data to identify bio-impacting relationships;
identifying a triggered event from the bio-impacting relationships, the triggered event being an event that results from a change in the bio-sensing data; and
performing an action in an attempt to cause a change in future bio-sensing data to prevent a future occurrence of the triggered event, the action being determined based at least in part on the triggered event.

31. The method of claim 30, further comprising:
processing the data to identify software application related data as having a first bio-impact; and
causing a future generation of the software application related data to cause the first bio-impact.

32. The method of claim 31, wherein the causing comprises at least one of: sending communications to remote devices, an offer to a user, a software reconfiguration, or a software selection.

33. The method of claim 30, wherein the data further comprises user interaction data, and the method further comprises gathering the data from at least one of the processing device or another device.

34. The method of claim 30, wherein the data further comprises device operational data, and the method further comprises:
processing the data to identify a predictive association between a first portion of the bio-sensing data and a first portion of the device operational data; and
causing a future generation of the device operational data after encountering future counterparts of the first portion of the bio-sensing data.

35. The method of claim 34, wherein the predictive association is between the first portion of the bio-sensing data, the first portion of the device operational data and non-bio-sensing context information.

36. A device comprising:
at least one processor configured to:
obtain an environmental profile of an environment associated with a user;
determine an expected biometric profile of the user based at least on the environmental profile;
obtain a current biometric profile of the user; and
perform an action to facilitate conforming the current biometric profile of the user to the expected biometric profile.

37. The device of claim 36, wherein the at least one processor is further configured to:
obtain another current biometric profile of another user; and
perform the action that is expected to facilitate conforming the current biometric profile of the user and the another current biometric profile of the another user to the expected biometric profile.

38. The device of claim 37, wherein the at least one processor is further configured to:
obtain the current biometric profile of the user by receiving biometric data from a sensor device, wherein the sensor device is coupled to the user; and
receive sensor data from at least one sensor device to obtain the environmental profile of the environment.

39. The device of claim 36, wherein the at least one processor is further configured to:
generate a user biometric model based at least on a plurality of recommended biometric profiles associated with a plurality of environment profiles, the plurality of recommended biometric profiles being adjusted based at least on historical biometric profile data of the user; and
determine the expected biometric profile of the user by applying the environmental profile to the user biometric model.

40. The device of claim 36, wherein the at least one processor is further configured to:
receive a plurality of biometric profiles of the user that are mapped to a plurality of behaviors of the user; and
determine a biometric profile adjustment for conforming the current biometric profile to the expected biometric profile,
wherein performing the action facilitates one of the plurality of behaviors of the user that is mapped to one of the plurality of biometric profiles that achieves the biometric profile adjustment.

41. The device of claim 36, wherein the environment is associated with additional users and the at least one processor is further configured to:
receive expected biometric profiles and current biometric profiles of the additional users from devices of the additional users; and
perform the action to facilitate conforming the current biometric profiles of the additional users and the user to the expected biometric profiles of the additional users and the user, respectively.

42. The device of claim 41, wherein the at least one processor is further configured to:
assimilate preferences of the additional users received from the devices of the additional users; and
perform the action to facilitate the conforming based at least in part on the assimilated preferences of the additional users.

43. The device of claim 42, wherein the at least one processor is further configured to:
determine a subset of the preferences that are shared by a threshold number of the additional users; and
perform the action to facilitate the conforming based at least in part on the subset of the preferences of the additional users.

44. The device of claim 42, wherein the at least one processor is further configured to:
provide, for display, the preferences of the additional users;
receive user input with respect to the displayed preferences of the additional users; and
perform the action to facilitate the conforming based at least in part on the received user input.

45. The device of claim 36, wherein the at least one processor is further configured to:
gather and store time-related data, the time-related data including bio-sensing data, user interaction data and software application data;
process the time-related data to identify bio-impacting relationships from which the expected biometric profile of the user is determinable;
identify the current biometric profile from the bio-sensing data; and
respond to the identification by performing the action in an attempt to alter future bio- sensing data.

46. The device of claim 36, wherein the at least one processor is further configured to:
store, with a timing relationship, first data, the first data including bio-sensing related data and software application related data gathered over a period of time;
process the first data to identify software application related data as having a first bio-impact; and
perform the action to cause a future generation of the software application related data to cause the first bio-impact in order to facilitate conforming the current biometric profile of the user to the expected biometric profile.

47. The device of claim 36, wherein the at least one processor is configured to conform the current biometric profile of the user to the expected biometric profile of the user comprises by maintaining the current biometric profile of the user.

48. The device of claim 36, wherein the at least one processor is further configured to:
store, with a timing relationship, gathered data, the gathered data including bio-sensing related data and device operational data collected over time;
process the gathered data to identify a predictive association between a first portion of the bio-sensing related data and a first portion of the device operational data; and
performing the action to cause a future generation of the device operational data in response to obtaining the current biometric profile of the user, wherein the current biometric profile of the user comprises future counterparts of the first portion of the bio-sensing related data.

49. The device of claim 48, wherein the action comprises at least one of sending a communication to a remote device, providing an offer to a user, performing a software reconfiguration, or performing a software selection.

50. The device of claim 48, wherein the at least one processor is further configured to:
process the gathered data to identify the predictive association between the first portion of the bio-sensing related data, the first portion of the device operational data, and at least one non-bio-sensing context information item.

* * * * *